(12) United States Patent
Farris

(10) Patent No.: US 9,987,338 B2
(45) Date of Patent: Jun. 5, 2018

(54) MITRECIN A POLYPEPTIDE WITH ANTIMICROBIAL ACTIVITY

(71) Applicant: The MITRE Corporation, McLean, VA (US)

(72) Inventor: Michael Heath Farris, Vienna, VA (US)

(73) Assignee: THE MITRE CORPORATION, McClean, VA (US)

( * ) Notice: Subject to any disclaimer, the term of this patent is extended or adjusted under 35 U.S.C. 154(b) by 0 days. days.

(21) Appl. No.: 15/400,707

(22) Filed: Jan. 6, 2017

(65) Prior Publication Data
US 2017/0189498 A1    Jul. 6, 2017

Related U.S. Application Data

(62) Division of application No. 14/828,127, filed on Aug. 17, 2015, now Pat. No. 9,562,255, which is a division of application No. 14/025,360, filed on Sep. 12, 2013, now Pat. No. 9,139,626.

(60) Provisional application No. 61/700,514, filed on Sep. 13, 2012.

(51) Int. Cl.
| | |
|---|---|
| *A61K 38/48* | (2006.01) |
| *A61K 9/00* | (2006.01) |
| *A61K 9/06* | (2006.01) |
| *C12N 9/52* | (2006.01) |
| *A01N 37/46* | (2006.01) |
| *A23L 2/52* | (2006.01) |
| *A23L 33/10* | (2016.01) |

(52) U.S. Cl.
CPC .............. *A61K 38/48* (2013.01); *A01N 37/46* (2013.01); *A23L 2/52* (2013.01); *A23L 33/10* (2016.08); *A61K 9/0014* (2013.01); *A61K 9/06* (2013.01); *C12N 9/52* (2013.01); *A23V 2002/00* (2013.01); *C07K 2319/00* (2013.01)

(58) Field of Classification Search
CPC ........... A01N 37/46; A23L 2/52; A23L 33/10; A23V 2002/00; A61K 38/48; A61K 9/0014; A61K 9/06; C07K 2319/00; C12N 9/52
See application file for complete search history.

(56) References Cited

U.S. PATENT DOCUMENTS

| | | | |
|---|---|---|---|
| 9,139,626 B2 | 9/2015 | Farris | |
| 9,562,255 B2 | 2/2017 | Farris | |
| 2010/0286030 A1 | 11/2010 | Farris | |
| 2014/0094401 A1 | 4/2014 | Farris | |
| 2016/0032349 A1 | 2/2016 | Farris | |

OTHER PUBLICATIONS

"Analysis and Cloning of Eukaryotic Genomic DNA," in *Molecular Cloning: A Laboratory Manual, Second Edition*, Sambrook, J., et al., Eds., pp. 9.47-9.57, Cold Spring Harbor Laboratory Press, New York, United States (1989).
Darquet, A-M., et al., "A new DNA vehicle for nonviral gene delivery: supercoiled minicircle," *Gene Therapy* 4:1341-1349, Stockton Press, England (1997).
Karlin, S. and Altschul, S.F., "Applications and statistics for multiple high-scoring segments in molecular sequences," *Proc. Natl. Acad. Sci. USA* 90:5873-5877, National Academy of Sciences, United States (1993).
Kim, B-J., et al., "Transferrin Fusion Technology: A Novel Approach to Prolonging Biological Half-Life of Insulinotropic Peptides," *The Journal of Pharmacology and Experimental Therapeutics* 334(3):682-692, American Society for Pharmacology and Experimental Therapeutics, United States (2010).
Nakamura, Y., et al., "Codon usage tabulated from international DNA sequence databases: status for the year 2000," *Nucleic Acids Research* 28(1):292, Oxford University Press, England (2000).
Stevens, R.C., "Design of high-throughput methods of protein production for structural biology," *Structure* 8(9):R177-R185, Elsevier Science Ltd., England (2000).
Tagg, J.R., et al., "Bacteriocins of Gram-Positive Bacteria," *Bacteriological Reviews* 40(3):722-756, American Society for Microbiology, United States (1976).
Zhou, R., et al., "A Dye Release Assay for Determination of Lysostaphin Activity," *Analytical Biochemistry* 171:141-144, Academic Press, Inc., United States (1988).
GenBank Accession No. YP_003819570, "phage endolysin [*Brevundimonas subvibrioides* ATCC 15264]," accessed at www.ncbi.nlm.nih.gov/protein/YP_003819570.1, version YP_003819570.1, last modified Jun. 10, 2013.
GenBank Accession No. YP_002588038, "hypothetical protein BBAL3_176 [*Brevundimonas* sp. BAL3]," accessed at www.ncbi.nlm.nih.gov/protein/YP_002588038.1?report—genpept, version YP_0002588038.1, last modified Jun. 16, 2009.
GenBank Accession No. ZP_03065132, "endolysin [*Shigella dysenteriae* 1012]," accessed at www.ncbi.nlm.nih.gov/protein/ZP_03065132.1?report=genpept, version ZP_03065132.1, last modified on Nov. 9, 2010.
GenBank Accession No. YP_002293134, "putative phage endolysin [*Escherichia coli* SE11]," accessed at www.ncbi.nlm.nih.gov/protein/YP_002293134.1, version YP_002293134.1, last modified on Aug. 27, 2013.

(Continued)

Primary Examiner — Hasan S Ahmed
Assistant Examiner — Erinne R Dabkowski
(74) Attorney, Agent, or Firm — Sterne, Kessler, Goldstein & Fox P.L.L.C.

(57) ABSTRACT

The present invention provides a Mitrecin A polypeptide useful in prevention and treatment of one or more bacteria. Also provided is a method to kill or prevent growth of one or more bacteria comprising contacting the one or more bacteria with a Mitrecin A polypeptide. The target bacteria can be selected from the group consisting of a Gram-positive bacterium, a Gram-negative bacterium, or both. In one embodiment, the present invention is drawn to a polynucleotide encoding a Mitrecin A polypeptide, a vector comprising the polynucleotide, a host cell comprising the polynucleotide, or a composition comprising the Mitrecin A polypeptide, the polynucleotide, the vector, or the host cell.

15 Claims, 9 Drawing Sheets

(56) References Cited

OTHER PUBLICATIONS

Oshima, K., et al., "Complete Genome Sequence and Comparative Analysis of the Wild-type Commensal *Escherichia coli* Strain SE11 Isolated from a Healthy Adult;" *DNA Research* 15:375-386, Oxford University Press, England (2008).

GenBank Accession No. NP_543082, "putative endolysin [*Enterobacteria* phage phiP27]," accessed at www.ncbi.nlm.nih.gov/protein/NP_543082.1, version NP_543082.1, last modified on Jul. 16, 2008.

Recktenwald, J. and Schmidt, H., "The Nucleotide Sequence of Shiga Toxin (Stx) 2e-Encoding Phage ΦP27 Is Not Related to other Stx Phage Genomes, but the Modular Genetic Structure Is Conserved," *Infection and Immunity* 70(4):1896-1908, American Society for Microbiology, United States (2002).

GenBank Accession No. AEP08879, "L-alanyl-D-glutamate peptidase [*Micavibrio aeruginosavorus* ARL-13]," accessed at www.ncbi.nlm.nih.gov/proteinfAEP08879.1, version AEP08879.1, last modified on Jan. 31, 2014.

Wang, Z., et al., "Genomic insights into an obligate epibiotic bacterial predator: *Micavibrio aeruginosavorus* ARL-13," *BMC Genomics* 12(453):1-12, BioMed Central Ltd., England (Sep. 2011).

Excerpted File History (through Jul. 17, 2015) of U.S. Appl. No. 14/025,360, Michael Heath Farris, filed Sep. 12, 2013.

Kulagina, N.V., et al., "Antimicrobial Peptides for Detection of Bacteria in Biosensor Assays," *Analytical Chemistry* 77(19):6504-6508, American Chemical Society, United States (2005).

UniProt, "UniProtKB F4R1U4 (F4R1U4_BREDI)," Protein: Endolysin, Gene: BDIM_19170, accessed at http://www.uniprot.org/uniprot/F4R1U4, version AEP08879.1, last modified on Jan. 20, 2016, 4 pages.

Figure 1. Zymogram showing bacteriocin activity from *Streptomyces* sp. strain 212 against *Y. pseudotuberculosis*

Isolate 212

~125 kDa

Figure 2. Phylogenetic relatedness of Streptomyces sp. Strain 212 to Other Streptomyces
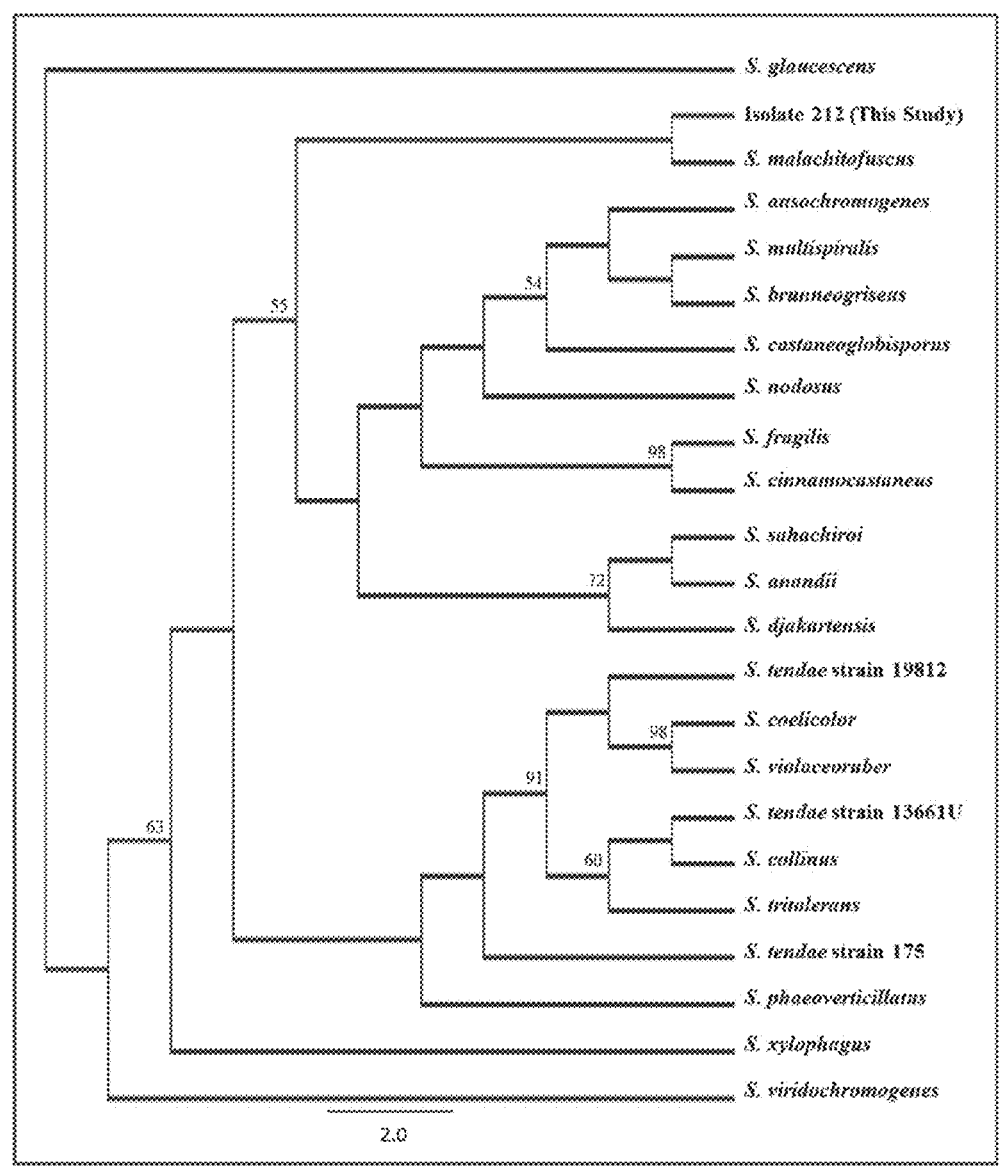

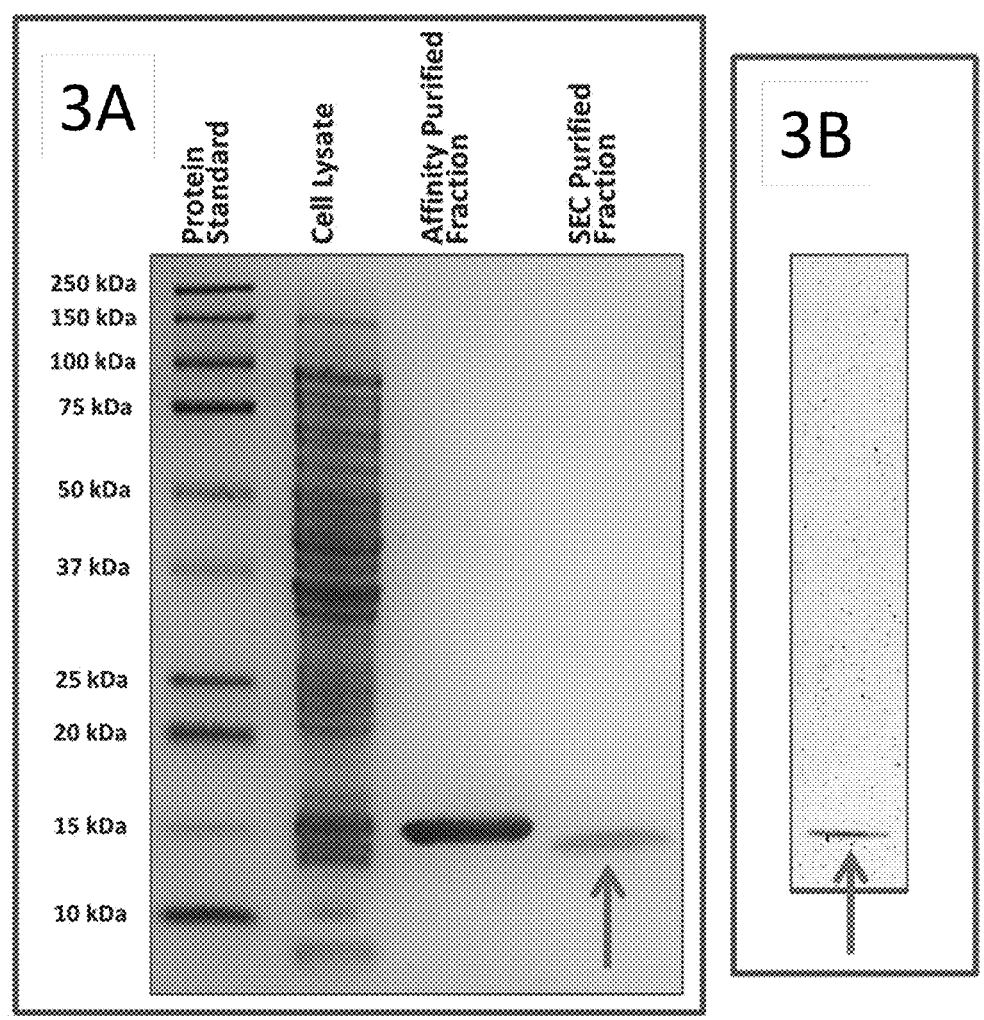
Figure 3A-3B. Preparation of Mitrecin A

Figure 4A. Relating Bacteriolytic Activity of Mitrecin A and Temperature
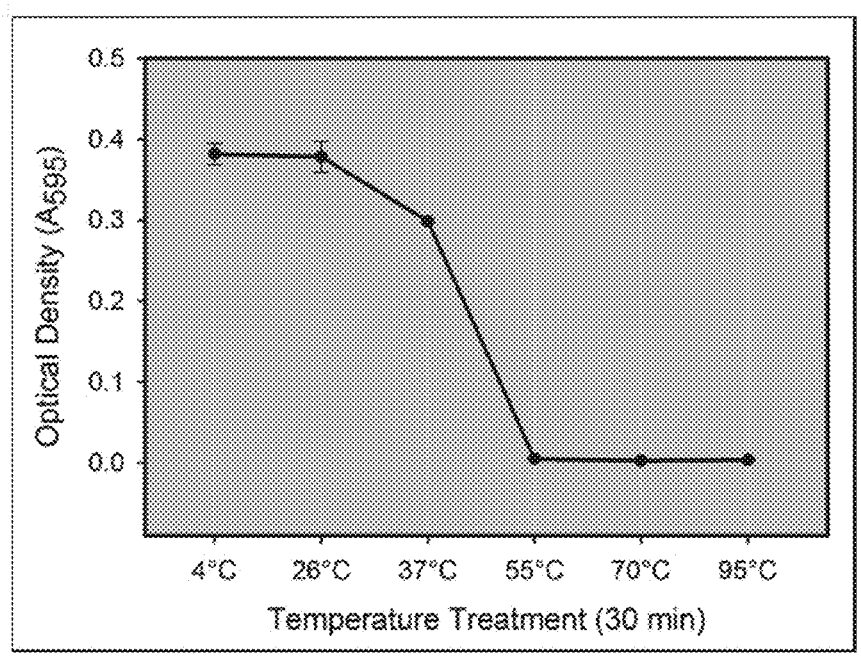

Figure 4B. Relating Bacteriolytic Activity of Mitrecin A and pH
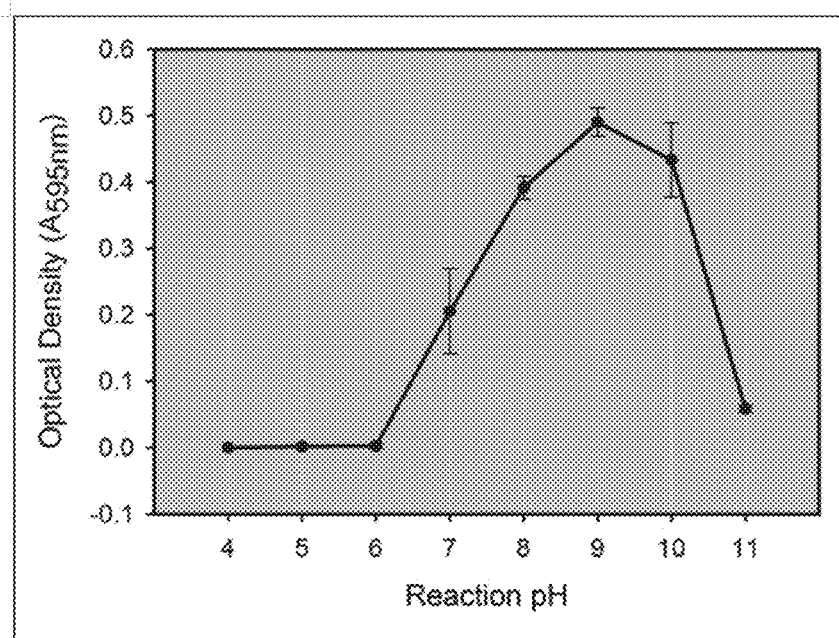

Figure 4C. Relating Bacteriolytic Activity of Mitrecin A and Salinity
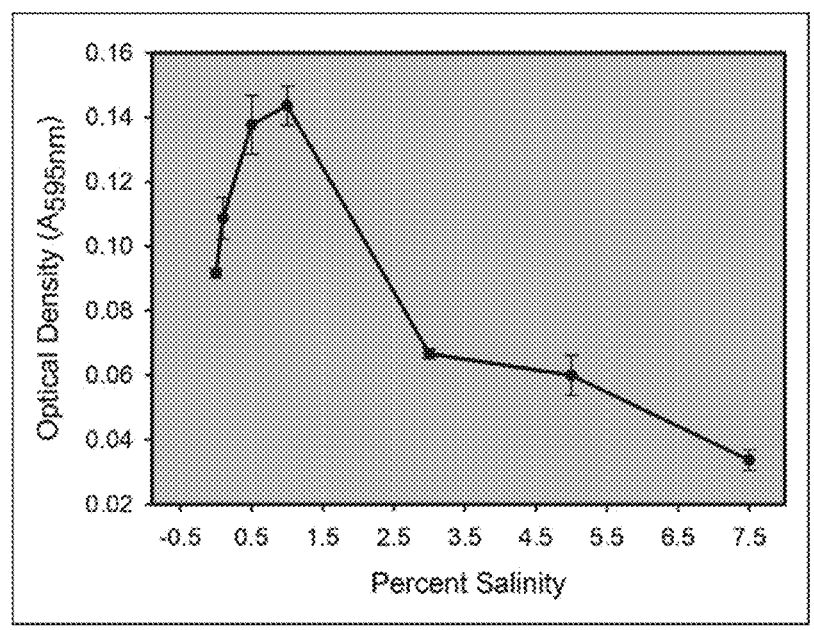

Figure 5. Mitrecin A Functional Assays
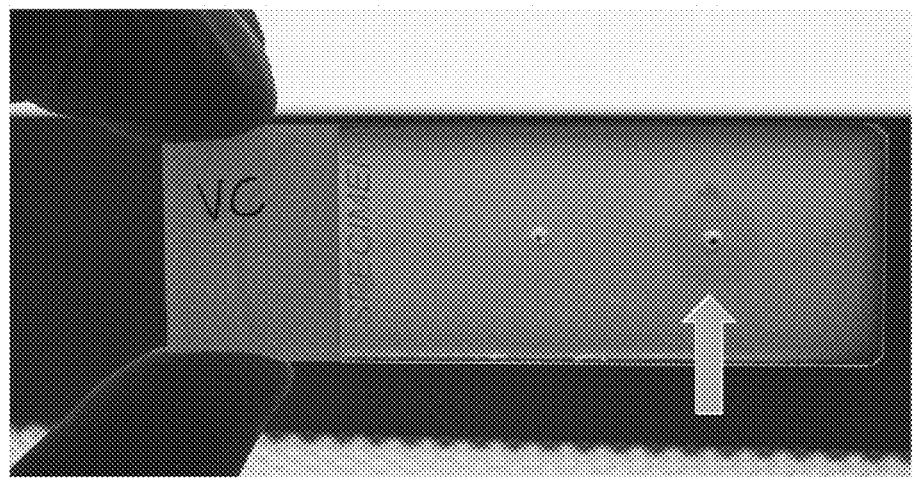

Figure 6. Bacteriolytic Activity of Mitrecin A against *Y. pseudutuberculosis*
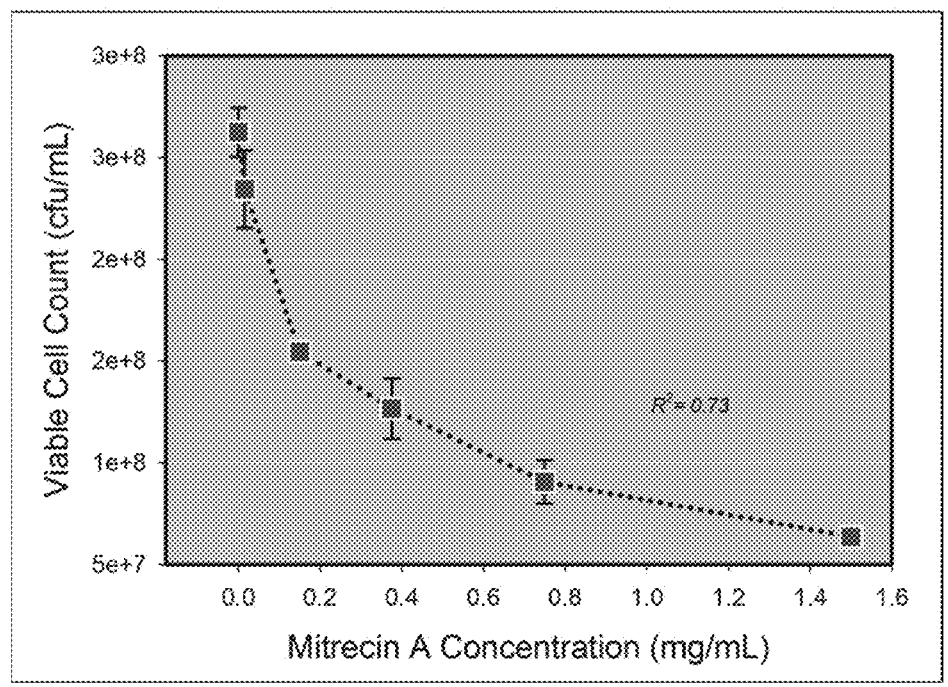

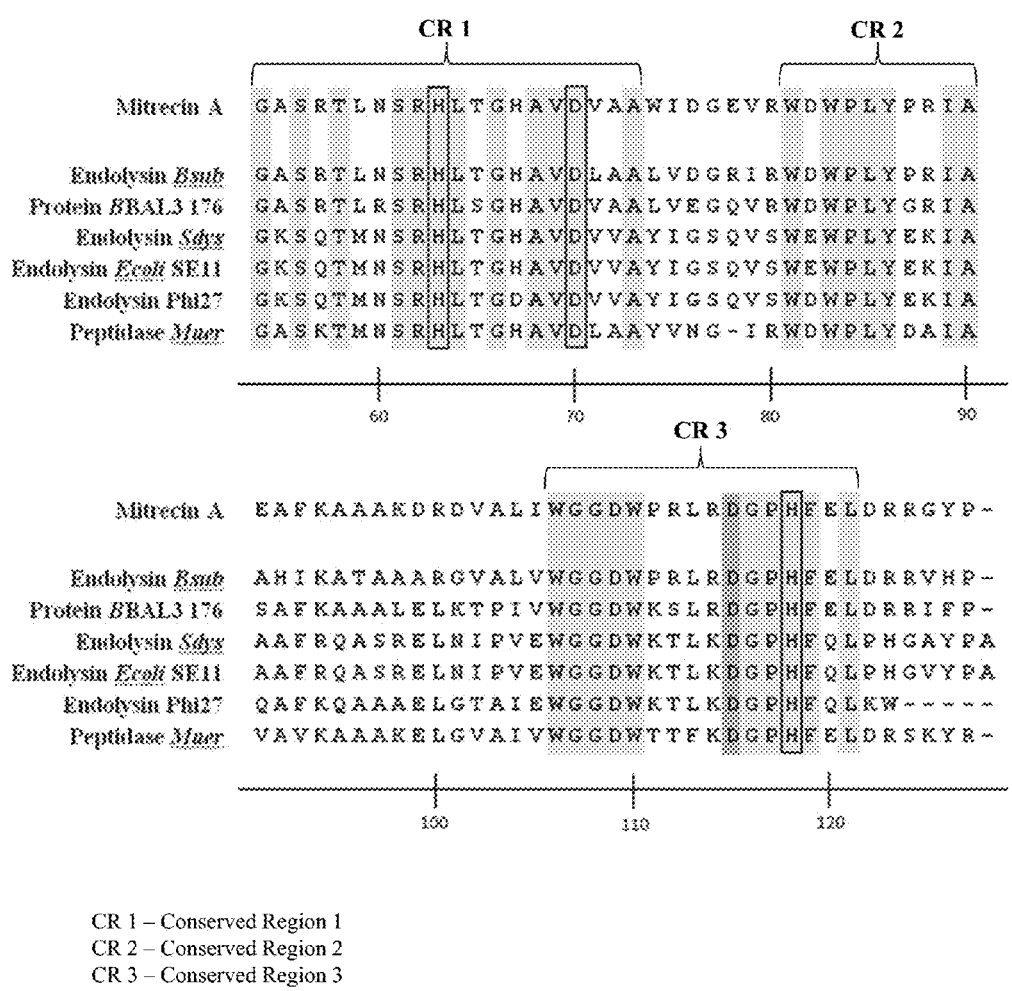
Figure 7. Conserved Regions of the Catalytic Region of Mitrecin A
CR 1 – Conserved Region 1
CR 2 – Conserved Region 2
CR 3 – Conserved Region 3

SEQUENCE LISTING

```
<160> NUMBER OF SEQ ID NOS: 11

<210> SEQ ID NO 1
<211> LENGTH: 384
<212> TYPE: DNA
<213> ORGANISM: Streptomyces sp. strain 212

<400> SEQUENCE: 1
atgagcttcg gtctgtcgca acgctcgcgc gagcggttga agggcgttca tcctgatctg      60
gtcgccgtgg tcgaggcggc gatccgcctg acgccggtgg acttcatgat cacagaggga     120
ttgcgcacgc ccgcgcgcca ggcggaactg gtccgcgcgg gggccagccg gacgctgaac     180
tcgcgccact tgacgggcca tgcggtggat gtcgccgcat ggatcgacgg cgaggtgcgc     240
tgggactggc cgctgtaccc ccgcatcgcc gaggcgttca aggcggcggc gaaggaccgg     300
gatgtggctc tgatctgggg cggcgactgg ccgcgcctgc gcgacggacc gcatttcgaa     360
ctggatcgga ggggctaccc atga                                            384

<210> SEQ ID NO 2
<211> LENGTH: 127
<212> TYPE: PRT
<213> ORGANISM: Streptomyces sp. strain 212

<400> SEQUENCE: 2

Met Ser Phe Gly Leu Ser Gln Arg Ser Arg Glu Arg Leu Lys Gly Val
1               5                   10                  15
```

```
His Pro Asp Leu Val Ala Val Glu Ala Ala Ile Arg Leu Thr Pro
            20                  25                  30

Val Asp Phe Met Ile Thr Glu Gly Leu Arg Thr Pro Ala Arg Gln Ala
         35                  40                  45

Glu Leu Val Arg Ala Gly Ala Ser Arg Thr Leu Asn Ser Arg His Leu
 50                  55                  60

Thr Gly His Ala Val Asp Val Ala Ala Trp Ile Asp Gly Glu Val Arg
 65                  70                  75                  80

Trp Asp Trp Pro Leu Tyr Pro Arg Ile Ala Glu Ala Phe Lys Ala Ala
                 85                  90                  95

Ala Lys Asp Arg Asp Val Ala Leu Ile Trp Gly Gly Asp Trp Pro Arg
            100                 105                 110

Leu Arg Asp Gly Pro His Phe Glu Leu Asp Arg Arg Gly Tyr Pro
        115                 120                 125

<210> SEQ ID NO 3
<211> LENGTH: 6
<212> TYPE: PRT
<213> ORGANISM: Artificial sequence
<220> FEATURE:
<223> OTHER INFORMATION: Synthetic

<400> SEQUENCE: 3

His His His His His His
1               5

<210> SEQ ID NO 4
<211> LENGTH: 16
<212> TYPE: PRT
<213> ORGANISM: Artificial sequence
<220> FEATURE:
<223> OTHER INFORMATION: Synthetic

<400> SEQUENCE: 4

Gly Gly Gly Ser Gly Gly Gly Ser Gly Gly Gly Ser Gly Gly Gly Ser
1               5                   10                  15

<210> SEQ ID NO 5
<211> LENGTH: 12
<212> TYPE: PRT
<213> ORGANISM: Artificial sequence
<220> FEATURE:
<223> OTHER INFORMATION: Synthetic

<400> SEQUENCE: 5

Pro Glu Ala Pro Thr Asp Pro Glu Ala Pro Thr Asp
1               5                   10

<210> SEQ ID NO 6
<211> LENGTH: 74
<212> TYPE: PRT
<213> ORGANISM: Artificial Sequence
<220> FEATURE:
<223> OTHER INFORMATION: Phage Endolysin for Bsub; NCBI YP_003819570.1
      aa 54-127

<400> SEQUENCE: 6

Gly Ala Ser Arg Thr Leu Asn Ser Arg His Leu Thr Gly His Ala Val
1               5                   10                  15

Asp Leu Ala Ala Leu Val Asp Gly Arg Ile Arg Trp Asp Trp Pro Leu
            20                  25                  30

Tyr Pro Arg Ile Ala Ala His Ile Lys Ala Thr Ala Ala Ala Arg Gly
```

```
                35                  40                  45

Val Ala Leu Val Trp Gly Gly Asp Trp Pro Arg Leu Arg Asp Gly Pro
     50                  55                  60

His Phe Glu Leu Asp Arg Arg Val His Pro
 65                  70

<210> SEQ ID NO 7
<211> LENGTH: 74
<212> TYPE: PRT
<213> ORGANISM: Artificial Sequence
<220> FEATURE:
<223> OTHER INFORMATION: Phage Endolysin for Protein BBAL3 176; NCBI
      YP_002588038.1 aa 54-127

<400> SEQUENCE: 7

Gly Ala Ser Arg Thr Leu Arg Ser Arg His Leu Ser Gly His Ala Val
 1               5                  10                  15

Asp Val Ala Ala Leu Val Glu Gly Gln Val Arg Trp Asp Trp Pro Leu
                 20                  25                  30

Tyr Gly Arg Ile Ala Ser Ala Phe Lys Ala Ala Ala Leu Glu Leu Lys
             35                  40                  45

Thr Pro Ile Val Trp Gly Gly Asp Trp Lys Ser Leu Arg Asp Gly Pro
     50                  55                  60

His Phe Glu Leu Asp Arg Arg Ile Phe Pro
 65                  70

<210> SEQ ID NO 8
<211> LENGTH: 75
<212> TYPE: PRT
<213> ORGANISM: Artificial Sequence
<220> FEATURE:
<223> OTHER INFORMATION: Phage Endolysin for Sdys; NCBI ZP_03065132.1
      aa 54-128

<400> SEQUENCE: 8

Gly Lys Ser Gln Thr Met Asn Ser Arg His Leu Thr Gly His Ala Val
 1               5                  10                  15

Asp Val Val Ala Tyr Ile Gly Ser Gln Val Ser Trp Glu Trp Pro Leu
                 20                  25                  30

Tyr Glu Lys Ile Ala Ala Ala Phe Arg Gln Ala Ser Arg Glu Leu Asn
             35                  40                  45

Ile Pro Val Glu Trp Gly Gly Asp Trp Lys Thr Leu Lys Asp Gly Pro
     50                  55                  60

His Phe Gln Leu Pro His Gly Ala Tyr Pro Ala
 65                  70                  75

<210> SEQ ID NO 9
<211> LENGTH: 75
<212> TYPE: PRT
<213> ORGANISM: Artificial Sequence
<220> FEATURE:
<223> OTHER INFORMATION: Phage Endolysin for Ecoli SE11; NCBI
      YP_002293134.1 aa 54-128

<400> SEQUENCE: 9

Gly Lys Ser Gln Thr Met Asn Ser Arg His Leu Thr Gly His Ala Val
 1               5                  10                  15

Asp Val Val Ala Tyr Ile Gly Ser Gln Val Ser Trp Glu Trp Pro Leu
                 20                  25                  30

Tyr Glu Lys Ile Ala Ala Ala Phe Arg Gln Ala Ser Arg Glu Leu Asn
             35                  40                  45
```

```
Ile Pro Val Glu Trp Gly Gly Asp Trp Lys Thr Leu Lys Asp Gly Pro
        50                  55                  60

His Phe Gln Leu Pro His Gly Val Tyr Pro Ala
65                  70                  75

<210> SEQ ID NO 10
<211> LENGTH: 70
<212> TYPE: PRT
<213> ORGANISM: Artificial Sequence
<220> FEATURE:
<223> OTHER INFORMATION: Phage Endolysin for Phi27; NCBI NP_543082.1
      aa 54-123

<400> SEQUENCE: 10

Gly Lys Ser Gln Thr Met Asn Ser Arg His Leu Thr Gly Asp Ala Val
1               5                   10                  15

Asp Val Val Ala Tyr Ile Gly Ser Gln Val Ser Trp Asp Trp Pro Leu
                20                  25                  30

Tyr Glu Lys Ile Ala Gln Ala Phe Lys Gln Ala Ala Glu Leu Gly
            35                  40                  45

Thr Ala Ile Glu Trp Gly Gly Asp Trp Lys Thr Leu Lys Asp Gly Pro
        50                  55                  60

His Phe Gln Leu Lys Trp
65                  70

<210> SEQ ID NO 11
<211> LENGTH: 73
<212> TYPE: PRT
<213> ORGANISM: Artificial Sequence
<220> FEATURE:
<223> OTHER INFORMATION: Phage Endolysin for Peptidase Maer; NCBI
      AEP08879.1 aa 54-126

<400> SEQUENCE: 11

Gly Ala Ser Lys Thr Met Asn Ser Arg His Leu Thr Gly His Ala Val
1               5                   10                  15

Asp Leu Ala Ala Tyr Val Asn Gly Ile Arg Trp Asp Trp Pro Leu Tyr
                20                  25                  30

Asp Ala Ile Ala Val Ala Val Lys Ala Ala Ala Lys Glu Leu Gly Val
            35                  40                  45

Ala Ile Val Trp Gly Gly Asp Trp Thr Thr Phe Lys Asp Gly Pro His
        50                  55                  60

Phe Glu Leu Asp Arg Ser Lys Tyr Arg
65                  70
```

US 9,987,338 B2

MITRECIN A POLYPEPTIDE WITH ANTIMICROBIAL ACTIVITY

CROSS REFERENCE TO RELATED APPLICATIONS

The following applications are incorporated by reference in their entirety: U.S. patent application Ser. No. 14/828,127, filed Aug. 17, 2015, now U.S. Pat. No. 9,562,255; U.S. patent application Ser. No. 14/025,360, filed Sep. 12, 2013, now U.S. Pat. No. 9,139,626; and U.S. Provisional Application No. 61/700,514, filed Sep. 13, 2012.

REFERENCE TO SEQUENCE LISTING SUBMITTED ELECTRONICALLY VIA EFS-WEB SECTION

The content of the electronically submitted sequence listing (Name: 2272_1810003_SeqListing_ST25.txt, Size: 7,461 bytes; and Date of Creation: Jan. 3, 2017) is submitted herewith and is incorporated herein by reference in its entirety.

BACKGROUND OF THE INVENTION

Field of Invention

Bacteriocins are defined as compounds produced by bacteria that have a biologically active protein moiety and bactericidal action (Tagg et al., Bacteriological Reviews, Volume 40, 722-256, 1976). Their characteristics may include: (1) a narrow inhibitory spectrum of anti-microbial activity among closely related species; (2) attachment to specific cell receptors; and/or (3) plasmid-borne genetic determinants of bacteriocin production and of host cell bacteriocin immunity. Their widespread occurrence in bacterial species isolated from complex microbial communities such as the intestinal tract, the oral or other epithelial surfaces, suggests that bacteriocins may have a regulatory role in terms of population dynamics within bacterial ecosystems.

Bacteriocins have commercial uses in the control of microbes such as extending the shelf life of foods, decreasing spoilage, and reducing the risk of exposure to food-borne pathogens. Additionally, as bacteriocins typically act on the cell membrane, there is no cross-resistance with approved and marketed antibiotics. Moreover, bacteriocins target prokaryotes and in some cases eukaryotes, making them safe for human consumption. Bacteriocins can also reduce the use of chemical preservatives, as well as facilitate the marketing of foods that are less acidic, have a lower salt content, or have a higher water content than foods now available.

To date, only one such bacteriocin, nisin, has been approved for use by the United States Food and Drug Administration (FDA) as an antimicrobial agent for use on casings for frankfurters and on cooked meat and poultry products. However, nisin-resistant *L. monocytogenes* strains have been reported. In addition, different bacteriocins have different spectra of bactericidal activity. Therefore, there is a need in the art for a safe, new broad-spectrum bacteriocin.

SUMMARY OF THE INVENTION

The present invention provides an isolated polypeptide comprising an amino acid sequence at least 90% identical to SEQ ID NO: 2 or a fragment thereof, wherein the polypeptide kills or inhibits growth of one or more bacteria (e.g., Mitrecin A). The one or more bacteria can be a Gram-positive bacterium, a Gram-negative bacterium, or both a Gram-positive bacterium and a Gram-negative bacterium. The one or more bacteria are, for example, *Vibrio cholerae, Shigella sonnei, Aeromonas hydrophila, Salmonella enterica, Yersinia pseudotuberculosis,* and *Bacillus subtilis.*

In one embodiment, the isolated polypeptide comprises an amino acid sequence at least 95%, 96%, 97%, 98%, 99%, or 100% identical to SEQ ID NO: 2. In another embodiment, the polypeptide comprises an amino acid sequence is encoded by a nucleotide sequence at least 80%, 85%, 90%, 95%, 96%, 97%, 98%, 99%, or 100% identical to SEQ ID NO: 1.

In some embodiment, the isolated polypeptide of the invention comprises Conserved Region 1 of SEQ ID NO: 2, wherein the polypeptide kills or inhibits growth of one or more bacteria. In one aspect, Conserved Region 1 comprises amino acids 54 to 73 of SEQ ID NO: 2. In another aspect, the polypeptide further comprises Conserved Region 2 (e.g., amino acids 81 to 90 of SEQ ID NO: 2). In other aspects, the polypeptide comprises Conserved Region 1, Conserved Region 2, and Conserved Region 3 (e.g., amino acids 106 to 121 of SEQ ID NO: 2). In some aspects, the polypeptide comprises amino acids 54 to 121 of SEQ ID NO: 2.

In certain embodiments, the polypeptide is conjugated to a heterologous moiety.

In other embodiments, the invention includes an isolated polynucleotide comprising a nucleic acid sequence encoding a Mitrecin A polypeptide. The polynucleotide sequence is at least 80%, 85%, 90%, 95%, 96%, 97%, 98%, 99%, or 100% identical to SEQ ID NO: 1.

In still other embodiments, the invention includes a vector comprising a Mitrecin A polynucleotide or a host cell comprising the vector.

In further embodiments, the invention provides a composition comprising a Mitrecin A polypeptide, a polynucleotide encoding a Mitrecin A polypeptide, or a Mitrecin A encoding vector. In a particular embodiment, the composition is a food preservative, a dietary supplement, a topical cream or lotion, a drink, a disinfectant, an antiseptic, a pill, a gargle, a wipe, or a chewing gum.

The invention also includes a method of killing or inhibiting growth of one or more bacteria comprising contacting the bacteria with an effective amount of a Mitrecin A polypeptide, a polynucleotide encoding the Mitrecin A polypeptide, a vector comprising the polynucleotide, a host cell comprising the vector, or a composition comprising the polypeptide, the polynucleotide, the vector, or the host cell of the present invention, wherein the polypeptide, the polynucleotide, the vector, the host cell, or the composition kills or inhibits growth of one or more bacteria. In one embodiment, the one or more bacteria are in a food system and are capable of spoiling the food system. In another embodiment, the one or more bacteria induce a disease or disorder in a plant or in an animal. For example, by contacting a Mitrecin A polypeptide, a polynucleotide encoding the Mitrecin A polypeptide, a vector comprising the polynucleotide, a host cell comprising the vector, or a composition comprising the polypeptide, the polynucleotide, the vector, or the host cell of the present invention with the one or more bacteria, the polypeptide, the polynucleotide, the vector, the host cell, or the composition prevents spoilage of the food system for a period longer than a food system having no contact with the polypeptide, the polynucleotide, the vector, the host cell, or the composition.

In some embodiments, the invention includes a method of preventing, ameliorating, or treating a disease or disorder in a plant comprising contacting the plant with an effective amount of a polypeptide, a polynucleotide encoding the Mitrecin A polypeptide, a vector comprising the polynucleotide, a host cell comprising the vector, or a composition comprising the polypeptide, the polynucleotide, the vector, or the host cell of the present invention prevents, ameliorates, or treats the disease or disorder in the plant. The disease or disorder in the plant can induce growth inhibition or retardation, less fruit formation, or a higher death rate of the plant compared to a plant without the disease or disorder. In one aspect, the plant is an agricultural crop. In another aspect, the contacting is spraying a Mitrecin A polypeptide, a polynucleotide encoding the Mitrecin A polypeptide, a vector comprising the polynucleotide, a host cell comprising the vector, or a composition comprising the polypeptide, the polynucleotide, the vector, or the host cell of the present invention on the plant or adding the polypeptide, the polynucleotide, the vector, the host cell, or the composition in the soil around the plant.

In other embodiments, the invention includes a method of preventing, ameliorating, or treating a disease or disorder in an animal comprising contacting the animal with an effective amount of a Mitrecin A polypeptide, a polynucleotide encoding the Mitrecin A polypeptide, a vector comprising the polynucleotide, a host cell comprising the vector, or a composition comprising the polypeptide, the polynucleotide, the vector, or the host cell of the present invention prevents, ameliorates, or treats the disease or disorder in the animal. For example, the contacting is ingesting of the Mitrecin A polypeptide, the polynucleotide, the vector, the host cell, or the composition by the animal or application of the polypeptide, the polynucleotide, the vector, the host cell, or the composition on a skin of the animal. In one aspect, the animal is a non-human animal. In another aspect, the animal is human.

In yet other embodiments, the invention is directed to a method of determining pathogenic bacteria in a sample comprising contacting the sample with an effective amount of a Mitrecin A polypeptide, a polynucleotide encoding a Mitrecin A polypeptide, a vector comprising the polynucleotide, a host cell comprising the vector, or a composition comprising the polypeptide. The method can further comprise measuring killing or growth inhibition of the pathogenic bacteria in the sample. In one example, the sample can be an environmental sample. In another example, the sample is a tissue of an animal or a plant.

The invention also includes a method of producing a polypeptide which kills or inhibits growth of one or more bacteria, the method comprising culturing a host cell comprising a polynucleotide encoding a Mitrecin A polypeptide of the invention under suitable conditions to express the Mitrecin A polypeptide.

BRIEF DESCRIPTION OF THE DRAWINGS

FIG. 1. Bacteriocin activity of *Streptomyces* sp. strain 212. Zymogram analysis of *Streptomyces* sp. strain 212 growth supernatant was used to measure its bacteriocin activity against *Y. pseudotuberculosis* impregnated in a SDS PAGE gel substrate.

FIG. 2. Neighbor-joining cladogram based on nearly complete 16S rRNA gene sequences showing the phylogenetic relationship between *Streptomyces* sp. strain 212 and other *Streptomyces* species. Percentages of bootstrap support (>50%) based on 1000 replications are shown at the nodes.

FIG. 3A-3B. FIG. 3A: Stepwise purification of a Mitrecin A 6-histidine fusion protein as shown by SDS-PAGE separation. The lane labeled "Protein Standard" contains molecular mass standards. The lane labeled "Cell Lysate" contains whole cell lysate of the heterologous expression host *E. coli* BL21 (DE3)pLysS. The lane labeled "Affinity Purified Fraction" contains metal affinity purified Mitrecin A fusion protein. Finally, the lane labeled "SEC Purified Fraction" contains Mitrecin A as purified by size exclusion chromatography. FIG. 3B: Western Blot Analysis against the 6x-His tag of purified Mitrecin A fusion protein. Arrows indicate purified Mitrecin A.

FIG. 4A-4C. Factors affecting Mitrecin A activity. Using a quantitative dye-release assay, residual bacteriolytic activity of Mitrecin A (1 µg) was measured (FIG. 4A) at various temp conditions after various 30-minute temperature treatments, (FIG. 4B) various pH concentrations, and (FIG. 4C) various saline concentrations.

FIG. 5. Slide diffusion assay measuring the bacteriolytic effects of Mitrecin A on indicator organisms. Right well contains 1 µg of Mitrecin A suspended in 10 µl Tris-HCl 50 mM NaCl buffer. Left well contains buffer with no enzyme. The slide was custom constructed with an overlay of agarose containing *Vibrio cholerae* cells. Slides were incubated at 37° C.

FIG. 6. Bacteriolytic effects of various concentrations of Mitrecin A against *Yersinia pseudotuberculosis*. Viable cell count assays were conducted after 16 h incubation at 37° C. in the presence of enzyme.

FIG. 7. Conserved Regions of the catalytic domain of Mitrecin A. The C-terminus of Mitrecin A (amino acids 54 to 127 of SEQ ID NO: 2) was aligned with the catalytic domains of closely related zinc metallohydrolases within the C-terminal VanY peptidase superfamily using ClustalW Multiple sequence alignment tool of BioEdit Sequence Alignment Editor. The conserved amino acid residues and motifs are shaded. Histidine (H) (amino acid residue 63 corresponding to SEQ ID NO: 2), aspartic acid (D) (amino acid residue 70 corresponding to SEQ ID NO: 2), and histidine (H) (amino acid residue 118 corresponding to SEQ ID NO: 2) residues inferred by analysis in the MEROPS database that may be necessary for interaction with the zinc ion within the binding pocket of the catalytic site are enclosed in boxes. The active site residue (aspartic acid (D) at amino acid residue 115 corresponding to SEQ ID NO: 2) as determined by analysis in MEROPS is also shaded. The catalytic domain of Mitrecin A contains three conserved regions (Conserved Region 1, Conserved Region 2, and Conserved Region 3). Conserved Region 1 comprises amino acids 54 to 73 of SEQ ID NO: 2. Conserved Region 2 comprises amino acids 81 to 90 of SEQ ID NO: 2. Conserved Region 3 comprises amino acids 106 to 121 of SEQ ID NO: 2. C-terminus domains of the sequences with similarity to Mitrecin A identified in MEROPS Blast searches and subsequently aligned against the Mitrecin A C-terminus include phage endolysin from *Brevundimonas subvibrioides* ATCC 15264 (Endolysin Bsub; NCBI YP_003819570.1, SEQ ID NO: 6), hypothetic protein BBAL3 176 from *Brevundimonas* sp. BAL3 (Protein BBAL3 176; NCBI YP_002588038.1, SEQ ID NO: 7), endolysin from *Shigella dysenteriae* strain 1012 (Endolysin Sdys; NCBI ZP_03065132.1, SEQ ID NO: 8), putative phage endolysin from *Escherichia coli* strain SE11 (Endolysin Ecoli SE11; NCBI YP_002293134.1, SEQ ID NO: 9), putative endolysin from *Enterobacteria* phase Phi27 (Endolysin Phi27; NCBI NP_543082.1, SEQ ID NIO: 10), and L-alanyl-D-glutamate peptidase from *Micavibrio aerugi-*

*nosavorus* strain ARL-13 (Peptidase Maer; NCBI AEP08879.1, SEQ ID NO: 11).

DETAILED DESCRIPTION OF THE INVENTION

The present invention is directed to polypeptides and polynucleotides that are capable of killing or inhibiting growth of one or more target bacterium and their uses in killing or inhibiting growth of one or more target bacterium.

Methods of making and using the present invention include all conventional techniques of molecular biology, microbiology, and recombinant DNA technology. Such techniques are set forth in the literature including but not limited to e.g. Sambrook Molecular Cloning; A Laboratory Manual, Second Edition (1989) and Third Edition (2001); Genetic Engineering: Principles and Methods, Volumes 1-25 (J. K. Setlow ed, 1988); DNA Cloning, Volumes I and II (D. N Glover ed. 1985); Oligonucleotide Synthesis (M. J. Gait ed, 1984); Nucleic Acid Hybridization (B. D. Hames & S. J. Higgins eds. 1984); Transcription and Translation (B. D. Hames & S. J. Higgins eds. 1984); Immobilized Cells and Enzymes (IRL Press, 1986); B. Perbal, A Practical Guide to Molecular Cloning (1984); the Methods in Enzymology series (Academic Press, Inc.), especially volumes 154 & 155; Scopes, (1987) Protein Purification: Principles and Practice, Second Edition (Springer-Verlag, N.Y.), and Handbook of Experimental Immunology, Volumes I-IV (D. M. Weir and C. C. Blackwell eds 1986). (Sambrook et al. (1989) Molecular Cloning: A Laboratory Manual 2nd ed., Cold Spring Harbor Laboratory Press and Ausubel et al. Eds. (1997) Current Protocols in Molecular Biology, John Wiley & Sons, Inc.).

Definitions

It is to be noted that the term "a" or "an" entity refers to one or more of that entity; for example, "a polypeptide," is understood to represent one or more polypeptides. As such, the terms "a" (or "an"), "one or more," and "at least one" can be used interchangeably herein.

The term "nucleic acid," "nucleotide," "nucleic acid fragment," or "nucleotide fragment" refers to any one or more nucleic acid segments, e.g., DNA or RNA fragments, present in a polynucleotide or construct. Two or more nucleic acids of the present invention can be present in a single polynucleotide construct, e.g., on a single plasmid, or in separate (non-identical) polynucleotide constructs, e.g., on separate plasmids. Furthermore, any nucleic acid or nucleic acid fragment may encode a single polypeptide, e.g., a single antigen, cytokine, or regulatory polypeptide, or may encode more than one polypeptide, e.g., a nucleic acid may encode two or more polypeptides. In addition, a nucleic acid may comprise a regulatory element such as a promoter or a transcription terminator, or may encode a specialized element or motif of a polypeptide or protein, such as a secretory signal peptide or a functional domain.

The term "polynucleotide" is intended to encompass a single nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349 (1997)) comprising a polynucleotide. A polynucleotide may be provided in linear (e.g., mRNA), circular (e.g., plasmid), or branched form as well as double-stranded or single-stranded forms. A polynucleotide may comprise a conventional phosphodiester bond or a non-conventional bond (e.g., an amide bond, such as found in peptide nucleic acids (PNA)).

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" may be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The terms "fragment" when referring to polypeptides of the present invention include any polypeptides which retain at least some of the antimicrobial activity of the original sequence (i.e., SEQ ID NO: 2). Fragments of Mitrecin A polypeptides of the present invention include proteolytic fragments, deletion fragments and fragments of a Mitrecin A polypeptides which exhibit increased solubility during expression or purification. In one example, a Mitrecin A polypeptide fragment comprises the catalytic domain of the full-length Mitrecin A polypeptide.

The term "analog," "derivative," or "variant," as used herein, can be used interchangeably and refers to a polypeptide that differs from the recited polypeptide due to amino acid substitutions, deletions, insertions, and/or modifications. Variants, derivatives, or analogs may occur naturally. Non-naturally occurring variants, analogs, or derivatives may be produced using art-known mutagenesis techniques. In one embodiment, variant, analog, or derivative polypeptides differ from an identified sequence by substitution, deletion or addition of five amino acids or fewer. Such variants may generally be identified by modifying a polypeptide sequence, and evaluating the antigenic properties of the modified polypeptide using, for example, the representative procedures described herein.

Polypeptide variants can exhibit at least about 60-70%, for example 75%, 80%, 85%, 90%, 94%, 95%, 96%, 97%, 98%, 99% or 99.9% sequence identity with identified polypeptides. Variant polypeptides may comprise conservative or non-conservative amino acid substitutions, deletions or additions. Examples include fusion proteins. An analog is another form of a polypeptide of the present invention.

Variants may also, or alternatively, contain other modifications, whereby, for example, a polypeptide may be conjugated or coupled, e.g., fused to a heterologous polypeptide, e.g., a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., 6-His), or to enhance binding of the polypeptide to a solid support. The polypeptide may also be conjugated or coupled to other polypeptides from another bacterium and/or other viruses to generate a hybrid protein that has antimicrobial activities to broader spectrum of pathogenic organisms.

Polypeptides, and fragments, derivatives, analogs, or variants thereof of the present invention can be bacteriocin polypeptides, which are used to kill or inhibit growth of one or more bacteria. The term "bacteriocin" as used herein refers to a substance that is capable of killing or inhibiting growth of one or more target bacteria when the substance comes in contact with the one or more bacteria.

As used herein, the term "isolated" means that the polynucleotide or polypeptide or fragment, variant, or derivative thereof has been removed from other biological materials with which it is naturally associated. An example of an isolated polynucleotide is a recombinant polynucleotide contained in a vector. Further examples of an isolated polynucleotide include recombinant polynucleotides maintained in heterologous host cells or purified (partially or substantially) polynucleotides in solution. Isolated RNA molecules include in vivo or in vitro RNA transcripts of the polynucleotides of the present invention. Isolated polynucleotides or nucleic acids according to the present invention further include such molecules produced synthetically.

As used herein, the term "purified" means that the polynucleotide or polypeptide or fragment, variant, or derivative thereof is substantially free of other biological material with which it is naturally associated, or free from other biological materials derived, e.g., from a recombinant host cell that has been genetically engineered to express the polypeptide of the invention.

The term "sequence identity" as used herein refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window (e.g., SEQ ID NO: 2). In order to optimally align sequences for comparison, the portion of a polynucleotide or polypeptide sequence in the comparison window may comprise additions or deletions termed gaps while the reference sequence (e.g. SEQ ID NO: 2) is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option.

The term "heterologous" refers to any additional biological components that are not identical with the subject biological component.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, and the like, are outside the coding region.

The term "codon optimization" is defined herein as modifying a nucleic acid sequence for enhanced expression in the cells of the host of interest by replacing at least one, more than one, or a significant number, of codons of the native sequence with codons that are more frequently or most frequently used in the genes of that host. Various species exhibit particular bias for certain codons of a particular amino acid.

An "effective amount" is the amount of which is sufficient to kill or inhibit growth of one or more bacteria or to detect or measure presence of one or more pathogenic bacteria. An amount is effective, for example, when its addition to or contact with the target bacteria results in the killing of the bacteria or reduction of the growth of the bacteria. This amount varies depending upon the condition of the target bacteria to be killed or inhibited, the number of the target bacteria, the family or species of the bacteria, the capacity of the food system or object that may contain the bacteria, the differences of the plant or animal to be protected, the degree of protection desired, and other relevant factors. It is expected that the effective amount will fall in a relatively broad range that can be determined through routine trials. Typically a single dose is from about 1 µg to 100 mg/ml of purified polypeptide.

The term "contacting" as used herein includes applying a Mitrecin A polypeptide to one or more bacteria or to an environment where bacteria are expected to grow, e.g., a hospital surface or water where bacteria are thought to be present. In one embodiment, "contacting" means mixing a Mitrecin A polypeptide with one or more bacteria in a container or on a surface on which one or more bacteria grow or may grow. In another embodiment, "contacting" means administering or applying a Mitrecin A polypeptide to a subject in need thereof that comes in contact with or is expected to come in contact with one or more bacteria.

"Treatment" refers to both therapeutic treatment and prophylactic or preventative measures, wherein the object is to prevent or slow down (lessen) the targeted pathologic condition or disorder, which is a condition or disorder caused by pathological bacteria, for example, Gram-positive pathological bacteria, more specifically staphylococci, and more specifically *Staphylococcus aureus*. Those in need of treatment include those already with the disorder as well as those prone to have the disorder or those for whom the disorder is to be prevented.

The term "non-human" is meant any animal other than human, particularly a livestock, for whom the protection from the target bacteria is desired. In one embodiment, the non-human animal is a non-human mammal. Mammalian subjects include, but are not limited to, domestic animals, farm animals, zoo animals such as bears, sport animals, pet animals such as dogs, cats, guinea pigs, rabbits, rats, mice, horses, cattle, bears, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In another embodiment, the animal is a human.

The term "animal" is intended to encompass a singular "animal" as well as plural "animals" and comprises mammals and birds, as well as fish, reptiles, and amphibians. The term animal also encompasses model animals, e.g., disease model animals. In some embodiments, the term animal includes valuable animals, either economically or otherwise, e.g., economically important breeding stock, racing animals, show animals, heirloom animals, rare or endangered animals, or companion animals. In particular, the mammal can be a human subject, a food animal or a companion animal.

Polypeptides

The present invention is drawn to a bacteriocin polypeptide or peptide referred to as a Mitrecin A polypeptide. The polypeptide of the invention is useful in killing or inhibiting growth of one or more target microorganisms and/or detecting the presence of one or more microorganisms. The polypeptide of the invention can be either bactericidal, bacteriostatic, or both. The polypeptide of the invention used as a bactericidal agent kills (e.g., is capable of killing) or destroys one or more bacteria. The polypeptide can thus be used as disinfectants, antiseptics, or antibiotics. The polypeptide of the invention used as a bacteriostatic agent inhibits growth of one or more bacteria from reproducing, while not necessarily harming them otherwise. Upon removal of the bacteriostatic agent, the bacteria can start to grow again.

In one embodiment, the invention is an isolated polypeptide comprising an amino acid sequence at least about 90% identical to SEQ ID NO: 2 or a fragment thereof, wherein the polypeptide kills or inhibits growth of one or more bacteria. The invention also includes a polypeptide comprising a functional fragment of SEQ ID NO: 2, wherein the polypeptide kills or inhibits growth of one or more bacteria. One example of the functional fragments of the full-length Mitrecin A polypeptide (i.e., SEQ ID NO: 2) is a polypeptide comprising a catalytic domain of the Mitrecin A polypeptide. In another embodiment, the invention is an isolated polypeptide consisting essentially of or consisting of an amino acid sequence at least about 90% identical to SEQ ID NO: 2 or a fragment thereof, wherein the polypeptide kills or inhibits growth of one or more bacteria. In one aspect, the polypeptide of the invention is bactericidal. In another aspect, the polypeptide of the invention is bacteriostatic. In some aspects, the polypeptide of the invention is both bactericidal and bacteriostatic. In some embodiments, the amino acid sequence in the polypeptide of the invention can be at least about 91%, 92%, 93%, 94%, 95%, 96%, 97%, 98%, or 99% identical to SEQ ID NO: 2. In certain embodiments, the amino acid sequence that is at least about 91%, 92%, 93%, 94%, 95%, 96%, 97%, 98%, or 99% identical to SEQ ID NO: 2 comprises histidine (H) at amino acid residue 63 corresponding to SEQ ID NO: 2, aspartic acid (D) at amino acid residue 70 corresponding to SEQ ID NO: 2, aspartic acid (D) at amino acid residue 115 corresponding to SEQ ID NO: 2, histidine (H) at amino acid residue 118 corresponding to SEQ ID NO: 2, or any combinations thereof. In other embodiments, the amino acid sequence that is at least about 91%, 92%, 93%, 94%, 95%, 96%, 97%, 98%, or 99% identical to SEQ ID NO: 2 comprises histidine (H) at amino acid residue 63 corresponding to SEQ ID NO: 2, aspartic acid (D) at amino acid residue 70 corresponding to SEQ ID NO: 2, aspartic acid (D) at amino acid residue 115 corresponding to SEQ ID NO: 2, and histidine (H) at amino acid residue 118 corresponding to SEQ ID NO: 2. In a particular embodiment, the amino acid sequence in the isolated polypeptide is SEQ ID NO: 2. In still other embodiments, the polypeptide of the invention comprises an amino acid sequence encoded by a nucleotide sequence at least about 80%, 85%, 90%, 95%, 96%, 97%, 98%, or 99% identical to SEQ ID NO: 1. In a particular embodiment, the polypeptide comprises an amino acid sequence encoded by SEQ ID NO: 2. An amino acid sequence of a Mitrecin A polypeptide and a nucleotide sequence encoding a Mitrecin A polypeptide are listed in Table 1.

TABLE 1

Amino Acid and Nucleotide Sequences of Mitrecin A.

| Identifier | Sequence |
| --- | --- |
| Amino acids of Mitrecin A (SEQ ID NO: 2) | MSFGLSQRSR ERLKGVHPDL VAVVEAAIRL TPVDFMITEG LRTPARQAEL VRAGASRTLN SRHLTGHAVD VAAWIDGEVR WDWPLYPRIA EAFKAAAKDR DVALIWGGDW PRLRDGPHFE LDRRGYP |
| Nucleic acids encoding Mitrecin A (SEQ ID NO: 1) | atgagcttcggtctgtcgcaacgctcgcgcga gcggttgaagggcgttcatcctgatctggtcg ccgtggtcgaggcggcgatccgcctgacgccg gtggacttcatgatcacagagggattgcgcac gcccgcgcgccaggcggaactggtccgcgcgg gggccagccggacgctgaactcgcgccacttg acgggccatgcggtggatgtcgccgcatggat cgacggcgaggtgcgctgggactggccgctgt acccccgcatcgccgaggcgttcaaggcggcg gcgaaggaccgggatgtggctctgatctgggg cggcgactggccgcgcctgcgcgacggaccgc atttcgaactggatcggaggggctacccatga |

Peptide and polypeptide sequences defined herein are represented by one-letter symbols for amino acid residues as follows: A (alanine); R (arginine); N (asparagine); D (aspartic acid); C (cysteine); Q (glutamine); E (glutamic acid); G (glycine); H (histidine); I (isoleucine); L (leucine); K (lysine); M (methionine); F (phenylalanine); P (proline); S (serine); T (threonine); W (tryptophan); Y (tyrosine); and V (valine).

Polynucleotides or nucleic acid sequences defined herein are represented by one-letter symbols for the bases as follows: A (adenine) C (cytosine) G (guanine) T (thymine) U (uracil) M (A or C) R (A or G) W (A or T/U); S(C or G); Y (C or T/U); K (G or T/U); V (A or C or G; not T/U); H (A or C or T/U; not G); D (A or G or T/U; not C); B (C or G or T/U; not A); N (A or C or G or T/U) or (unknown).

Also provided is an isolated polypeptide comprising an amino acid sequence at least about 90% identical to SEQ ID NO: 2 or a fragment thereof, wherein the amino acid sequence has a molecular weight of about 14 kDa as visualized by SDS-PAGE. In one embodiment, the polypeptide is capable of killing or inhibiting the growth of Gram-positive or Gram-negative target bacteria.

The present invention also includes an isolated polypeptide comprising full-length or mature Mitrecin A polypeptides as well as an isolated polypeptide comprising analogs, variants, derivatives, or fragments of the Mitrecin A polypeptides described herein. In one embodiment, the analogs, variants, derivatives, or fragments of the Mitrecin A polypeptide are capable of killing or inhibiting growth of one or more bacteria. In another embodiment, the analogs, variants, derivatives, or fragments of the Mitrecin A polypeptide are capable of specifically binding to an antibody raised against a polypeptide consisting of SEQ ID NO: 2 or a fragment thereof or an antibody raised against a polypeptide consisting of amino acids 54 to 121 of SEQ ID NO: 2. In other embodiments, the analogs, variants, derivatives, or fragments of the Mitrecin A polypeptide are capable of interacting with a zinc ion.

In one embodiment, a Mitrecin A polypeptide comprises, consists essentially thereof, or consists of a catalytic domain of the Mitrecin A polypeptide. The catalytic domain of the Mitrecin A polypeptide has conserved regions and key residues involved in facilitating the catalytically active site of the zinc metalloenzyme. The catalytic domain of the Mitrecin A polypeptide can comprise amino acids 54 to 121 of SEQ ID NO: 2. In another embodiment, a Mitrecin A polypeptide comprises an amino acid sequence at least 80%, 85%, 90%, 95%, 96%, 97%, 98%, 99%, or 100% identical to amino acids 54 to 121 of SEQ ID NO: 2. As one of skill in the art will appreciate, the beginning and ending residues of the domains may vary depending upon the computer modeling program used or the method used for determining the domains.

The catalytic domain of Mitrecin A comprises three highly conserved regions. The three conserved regions of the catalytic domain are shown in Table 2.

TABLE 2

Mitrecin A Conserved Regions

| Conserved region 1 | Conserved region 2 | Conserved region 3 |
| --- | --- | --- |
| Amino acids 54 to 73 of SEQ ID NO: 2 | Amino acids 81 to 90 of SEQ ID NO: 2 | Amino acids 106 to 121 of SEQ ID NO: 2 |

In one embodiment, an isolated polypeptide of the invention comprises Conserved Region 1 (e.g., amino acids 54 to 73 of SEQ ID NO: 2), Conserved Region 2 (e.g., amino acids 81 to 90 of SEQ ID NO: 2), or Conserved Region 3 (e.g., amino acids 106 to 121 of SEQ ID NO: 2). In another embodiment, an isolated polypeptide of the invention comprises Conserved Region 1 and Conserved Region 2, Conserved Region 2 and Conserved Region 3, Conserved Region 1 and Conserved Region 3, or Conserved Region 1, Conserved Region 2, and Conserved Region 3. In other embodiments, an isolated polypeptide of the invention comprises amino acids 54 to 90 of SEQ ID NO: 2, amino acids 81 to 121 of SEQ ID NO: 2, or amino acids 54 to 121 of SEQ ID NO: 2. In some embodiments, an isolated polypeptide of the invention comprises amino acids 54 to 127 of SEQ ID NO: 2. The isolated polypeptides of the invention comprising one or more Conserved Regions are capable of killing or inhibiting growth of one or more bacteria, specifically binding to an antibody raised against a polypeptide consisting of SEQ ID NO: 2 or a fragment thereof or a polypeptide consisting of amino acids 54 to 121 of SEQ ID NO: 2, or interacting with a zinc ion.

In certain embodiments, the present invention includes a polypeptide comprising at least two catalytic domains, at least three catalytic domains, at least four catalytic domains, or at least five catalytic domains derived from the Mitrecin A polypeptide.

Examples of Gram-positive target bacteria that can be killed or inhibited by the polypeptides of the present invention include, but are not limited to, Streptomyces avermitilis, Streptomyces coelicolor, Streptomyces lividans, Streptomyces venezuelae, Nocardia salmonicida, Nocardia vaccinii, Rhodococcus marinonascens, Bacillus megaterium, Bacillus subtilis, Bacillus cereus, Enterococcus faecalis, Micrococcus luteus, Staphylococcus aureus, Streptococcus sp., Streptococcus pyogenes, Listeria monocytogenes, Clostridium perfringens, Clostridium botulinum, Lactococcus cremoris, Lactobacillus sp., and Leuconostoc sp. Thus, a Gram-positive target bacterium can be selected from the group consisting of Streptomyces avermitilis, Streptomyces coelicolor, Streptomyces lividans, Streptomyces venezuelae, Nocardia salmonicida, Nocardia vaccinii, Rhodococcus marinonascens, Bacillus megaterium, Bacillus subtilis, Bacillus cereus, Enterococcus faecalis, Micrococcus luteus, Staphylococcus aureus, Streptococcus sp., Streptococcus pyogenes, Listeria monocytogenes, Clostridium perfringens, Clostridium botulinum, Lactococcus cremoris, Lactobacillus sp., and Leuconostoc sp.

Examples of Gram-negative target bacteria that can be killed or inhibited by the polypeptides of the present invention include, but are not limited to, Escherichia coli, Klebsiella pneumoniae, Salmonella typhimurium, Salmonella enterica, Campylobacter jejuni, Yersinia enterocolitica, Yersinia pseudotuberculosis, Vibrio cholerae, Vibrio parahaemolyticus, Vibrio vulnificus, Aeromonas hydrophila, Plesiomonas shigelloides, Shigella sonnei, Shigella flexneri, Enterobacter aerogenes, Flavobacterium sp., Acinetobacter sp., and Proteus sp. Thus, a Gram-negative target bacterium can be selected from the group consisting of Escherichia coli, Klebsiella pneumoniae, Salmonella typhimurium, Salmonella enteritidis, Campylobacter jejuni, Yersinia enterocolitica, Yersinia pseudotuberculosis, Vibrio cholerae, Vibrio parahaemolyticus, Vibrio vulnificus, Aeromonas hydrophila, Plesiomonas shigelloides, Shigella sonnei, Shigella flexneri, Enterobacter aerogenes, Flavobacterium sp., Acinetobacter sp., and Proteus sp.

In some embodiments, the target bacterium is Vibrio sp., Salmonella sp., Yersinia sp., Shigella sp. Aeromonas sp., or Bacillus sp. In a particular embodiment, the target bacterium is Vibrio cholerae, Salmonella enterica, Yersinia pseudotuberculosis, Shigella sonnei, Aeromonas hydrophila, or Bacillus subtilis.

In yet other embodiments, the target bacterium does not kill or inhibit growth of the cell line comprising a polynucleotide encoding a Mitrecin A polypeptide.

In other embodiments, the present invention includes a fusion polypeptide fused with a heterologous moiety. The heterologous moiety fused to a Mitrecin A polypeptide or a fragment, variant, analog, or derivative thereof can be a heterologous polypeptide, a non-polypeptide moiety, or both. The heterologous polypeptide can be translated from various heterologous nucleic acids. Various heterologous polypeptides can be used, and can be selected from the group consisting of an N- or C-terminal peptide imparting stabilization, secretion, or simplified purification, i.e., His-tag (SEQ ID NO: 3), ubiquitin tag, NusA tag, chitin binding domain, ompT, ompA, pelB, DsbA, DsbC, c-myc, KSI, polyaspartic acid, (Ala-Trp-Trp-Pro)n, polyphenyalanine, polycysteine, polyarginine, B-tag, HSB-tag, green fluorescent protein (GFP), hemagglutinin influenza virus (HAI), calmodulin binding protein (CBP), galactose-binding protein, maltose binding protein (MBP), cellulose binding domains (CBD's), dihydrofolate reductase (DHFR), glutathione-S-transferase (GST), streptococcal protein G, staphylococcal protein A, T7gene10, avidin/streptavidin/Strep-tag, trpE, chloramphenicol acetyltransferase, lacZ (β-Galactosidase), His-patch thioredoxin, thioredoxin, FLAG™ peptide (Sigma-Aldrich), S-tag, and T7-tag. See e.g., Stevens, R. C., Structure, 8:R177-R185 (2000). The heterologous polypeptides can further include any pre- and/or pro-sequences that facilitate the transport, translocations, processing and/or purification of the Mitrecin A polypeptide from a host cell. In some embodiments, the heterologous moiety comprises one or more bacteriocins (either native proteins or variants, fragments, or derivatives thereof, e.g., nisin).

Optionally, a Mitrecin A polypeptide fused with a heterologous polypeptide or other bacteriocin polypeptide can include a peptide linker sequence joining sequences that comprise two or more sequences having antimicrobial activities. Suitable peptide linker sequences may be chosen based on their ability to adopt a flexible, extended conformation, or a secondary structure that could interact with joined sequences, or based on their ability to increase overall solubility of the fusion polypeptide, or based on their lack of electrostatic or water-interaction effects that influence joined sequences. A linker sequence, (GGGS)$_n$ (SEQ ID NO: 4), where n can be 0, 1, 2, 3, 4, or more, can be added at N-terminal and/or C-terminal of the Mitrecin A polypeptide. Alternative linkers such as PEAPTDPEAPTD (SEQ ID NO: 5) can also be employed in place of GGGS linker (Kim et al., *J Pharmacol. Exp. Ther.*, 2010, 334, 682-692).

In some embodiments, the polypeptides of the present invention are isolated. No particular level of purification is required. Recombinantly produced endolysin polypeptides and proteins expressed in host cells are considered isolated for purposes of the invention, as are native or recombinant endolysin polypeptides which have been separated, fractionated, or partially or substantially purified by any suitable technique, including by filtration, chromatography, centrifugation, and the like.

In other embodiments, the polypeptides of the invention are at least 50%, at least 60%, at least 70%, at least 80%, at least 90%, at least 95%, at least 96%, at least 97%, at least 98%, at least 99%, or at least 100% purified.

In certain embodiments, the invention provides an antibody specifically binds to a Mitrecin A polypeptide. An anti-Mitrecin A antibody can be a monoclonal antibody or a polyclonal antibody. In further embodiments, the invention also includes an anti-serum raised against a polypeptide consisting of SEQ ID NO: 2 or a fragment thereof. The anti-Mitrecin A antibody or antiserum can be used to detect or purify a Mitrecin A polypeptide.

Polynucleotides

The present invention also includes a polynucleotide comprising a nucleic acid encoding a full-length Mitrecin A polypeptide or, fragment, analog, derivative, or variant thereof or a complementary sequence thereof.

Polynucleotide sequences encoding Mitrecin A polypeptides may be cloned from genomic DNA from *Streptomyces* sp. 212 by a variety of techniques known in the art. For instance, *Streptomyces* sp. 212 can be cultured as a cell culture as described in the art. *Streptomyces* sp. 212 genomic DNA can be isolated, for example, as described in the art. Full length Mitrecin A genes may be cloned, for example, by PCR amplification. Suitable primers are described herein, or may be designed using techniques well known in the art. An oligonucleotide forward primer, encoding a known N-terminal sequence of Mitrecin A, may be used together with an oligonucleotide reverse primer, which comprises the reverse complement of a known C-terminal sequence. Suitable primers may include a synthetic restriction enzyme cleavage site which is not found within the Mitrecin A coding sequence, to facilitate manipulation of the PCR amplification clone. Alternatively, degenerate primers may be designed which permit amplification of corresponding genes despite a high degree of sequence variability. PCR conditions can also be modified to allow for a greater degree of sequence similarity, as is well known to those skilled in the art.

Included within the scope of the invention are polynucleotides at least about 60%, 70%, 75%, 80%, 85%, 90%, 95%, 96%, 97%, 98%, 99% or 100% identical to polynucleotides encoding Mitrecin A polypeptides, fragments, derivatives, or variants thereof. In one aspect, the Mitrecin A polypeptides, fragments, derivatives, or variants thereof are capable of killing or inhibiting growth of one or more bacteria or are capable of specifically binding to an antibody raised against a polypeptide consisting of SEQ ID NO: 2 or a fragment thereof or a polypeptide consisting of amino acids 54 to 121 of SEQ ID NO: 2. In another aspect, the Mitrecin A polypeptides, fragments, derivatives, or variants thereof are capable of interacting with a zinc ion. Variants commonly occur with many genes of simple, unicellular organisms. Examples of variants can be found among natural variants. Another example of variants can be found within strains.

In one embodiment, the present invention includes a polynucleotide comprising, consisting essentially of, or consisting of a nucleic acid encoding an amino acid sequence at least about 80%, 85%, 90%, 95%, 96%, 97%, 98%, 99%, or 100% identical to amino acids 54 to 127 of SEQ ID NO: 2. In another embodiment, a polynucleotide encoding a Mitrecin A polypeptide comprises a nucleotide sequence encoding an amino acid sequence comprising (1) Conserved Region 1, (2) Conserved Region 2, (3) Conserved Region 3, (4) Conserved Region 1 and Conserved Region 2, (5) Conserved Region 1 and Conserved Region 3, (6) Conserved Region 2 and Conserved Region 3, or (7) Conserved Region 1, Conserved Region 2, and Conserved Region 3. In other embodiments, a polynucleotide of the invention comprises a nucleotide sequence encoding amino acids 54 to 90 of SEQ ID NO: 2, amino acids 81 to 121 of SEQ ID NO: 2, amino acids 54 to 121 of SEQ ID NO: 2, or amino acids 54 to 127 of SEQ ID NO: 2.

In other embodiments, a polynucleotide of the invention comprises a nucleotide sequence encoding an amino acid sequence at least about 90%, 95%, 96%, 97%, 98%, 99%, or 100% identical to SEQ ID NO: 2, wherein the amino acid sequence is capable of killing or inhibiting growth of one or more bacteria or is capable of specifically binding to an antibody raised against a polypeptide consisting of SEQ ID NO: 2 or a fragment thereof or a polypeptide consisting of amino acids 54 to 121 of SEQ ID NO: 2. In certain embodiments, a polynucleotide of the invention comprises a nucleotide sequence at least 70%, 80%, 90%, 91%, 92%, 93%, 94%, 95%, 96%, 97%, 98%, or 99% identical to SEQ ID NO: 1, wherein the amino acid sequence encoded by the nucleotide sequence is capable of killing or inhibiting growth of one or more bacteria or is capable of specifically binding to an antibody raised against a polypeptide consisting of SEQ ID NO: 2 or a fragment thereof or a polypeptide consisting of amino acids 54 to 121 of SEQ ID NO: 2. In other embodiments, the nucleotide sequence comprises nucleic acids encoding histidine (H) at amino acid residue 63 corresponding to SEQ ID NO: 2, aspartic acid (D) at amino acid residue 70 corresponding to SEQ ID NO: 2, aspartic acid (D) at amino acid residue 115 corresponding to SEQ ID NO: 2, histidine (H) at amino acid residue 118 corresponding to SEQ ID NO: 2, or any combinations thereof. In other embodiments, the nucleotide sequence that is at least about 70%, 80%, 90%, 91%, 92%, 93%, 94%, 95%, 96%, 97%, 98%, or 99% identical to SEQ ID NO: 1 comprises nucleic acids encoding histidine (H) at amino acid residue 63 corresponding to SEQ ID NO: 2, aspartic acid (D) at amino acid residue 70 corresponding to SEQ ID NO: 2, aspartic acid (D) at amino acid residue 115 corresponding to SEQ ID NO: 2, and histidine (H) at amino acid residue 118 corresponding to SEQ ID NO: 2. In a particular embodiment, the nucleotide sequence in the isolated polynucleotide is SEQ ID NO: 1.

In some embodiments of the present invention the polynucleotide is isolated. In other embodiments, the polynucleotide is purified. For example, a purified polypeptide of the present invention includes a polypeptide that is at least 70-100% pure, i.e., a polypeptide which is present in a composition wherein the polypeptide constitutes 70-100% by weight of the total composition. In some embodiments, the purified polypeptide of the present invention is 75%-99% by weight pure, 80%-99% by weight pure, 90-99% by weight pure, or 95% to 99% by weight pure. An example of an isolated polynucleotide is a recombinant polynucleotide contained in a vector. Further examples of an isolated polynucleotide include recombinant polynucleotides maintained in heterologous host cells or purified (partially or substantially) polynucleotides in solution. Isolated RNA molecules include in vivo or in vitro RNA transcripts of the polynucleotides of the present invention. Isolated polynucleotides or nucleic acids according to the present invention further include such molecules produced synthetically. The relative degree of purity of a polynucleotide or polypeptide of the invention is easily determined by well-known methods.

In some embodiments, the present invention is directed to a polynucleotide encoding Mitrecin A further comprising a heterologous nucleic acid. The heterologous nucleic acid can, in some embodiments, encode a heterologous polypeptide fused to a Mitrecin A polypeptide. The components may be host cells, genes, or regulatory regions, such as promoters. The heterologous components can function together, as when a promoter heterologous to a gene is operably linked to the gene. An example would be two epitopes from the same or different proteins which have been assembled in a single protein. Another example includes a polynucleotide which encodes an Fc portion of an antibody linked to a Mitrecin A polypeptide of the invention or a fragment thereof. A further example is a full-length or mature Mitrecin A polypeptide fused to a 6 histidine tag, i.e., SEQ ID NO: 3. The present invention includes a polynucleotide comprising a nucleic acid which encodes an amino acid sequence at least 70%, 75%, 80%, 85%, 90%, 95%, 99%, or 100% identical to SEQ ID NO: 2 without a signal sequence and a heterologous polypeptide, e.g., SEQ ID NO: 3, wherein said polypeptide is capable of killing or inhibiting growth of one or more bacteria.

Various heterologous nucleic acids can be used to encode their respective heterologous polypeptides. In some embodiments, the heterologous polypeptide is fused to the polypeptide of the present invention. Examples of the heterologous polypeptide that can be encoded by the heterologous polynucleotides are disclosed elsewhere herein.

Also included within the scope of the invention are genetically engineered polynucleotides encoding Mitrecin A variants. Modifications of nucleic acids encoding Mitrecin A polypeptides can readily be accomplished by those skilled in the art, for example, by oligonucleotide-directed site-specific mutagenesis of a polynucleotide coding for a Mitrecin A polypeptide. Such modified polypeptide can be encoded by a codon optimized nucleotide sequence. Such modifications impart one or more amino acid substitutions, insertions, deletions, and/or modifications to expressed Mitrecin A polypeptides including fragments, variants, and derivatives. Such modifications may enhance the antimicrobial activity of Mitrecin A polypeptides, for example. Such modification may enhance solubility of the polypeptides. Alternatively, such modifications may have no effect.

As appreciated by one of ordinary skill in the art, various nucleic acid coding regions will encode the same polypeptide due to the redundancy of the genetic code. Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 3. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the polypeptides encoded by the DNA.

TABLE 3

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Ter | TGA Ter |
|   | TTG Leu (L) | TCG Ser (S) | TAG Ter | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

It is to be appreciated that any polynucleotide that encodes a polypeptide in accordance with the invention falls within the scope of this invention, regardless of the codons used. The codon usage is adapted for optimized expression in the cells of a given prokaryote or eukaryote.

The polynucleotides encoding Mitrecin A are prepared by incorporating codons preferred for use in the genes of a given species into the DNA sequence. Also provided are polynucleotide expression constructs, vectors, host cells comprising nucleic acid fragments of codon-optimized coding regions which encode Mitrecin A polypeptides, and various methods of using the polynucleotide expression constructs, vectors, host cells to kill or prevent growth of one or more bacteria.

Given the large number of gene sequences available for a wide variety of animal, plant and microbial species, it is possible to calculate the relative frequencies of codon usage. Codon usage tables are readily available, for example, at the "Codon Usage Database" available at www.kazusa.or.jp/codon/ (visited May 30, 2006), and these tables can be adapted in a number of ways. See Nakamura, Y., et al., "Codon usage tabulated from the international DNA sequence databases: status for the year 2000" *Nucl. Acids Res.* 28:292 (2000). Codon usage tables for humans, *Escherichia coli*, and *P. fluorescens* calculated from GenBank Release 151.0, are reproduced below as Tables 10-12 (from www.kazusa.or.jp/codon/supra). These tables use mRNA nomenclature, and so instead of thymine (T) which is found in DNA, the tables use uracil (U) which is found in RNA. The tables have been adapted so that frequencies are calculated for each amino acid, rather than for all 64 codons.

DNA Synthesis A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

DNA Hybridization

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or Blotto); concentration of the sequences; use of compounds to increase the rate of association of sequences (dextran sulfate or polyethylene glycol); and the stringency of the washing conditions following hybridization.

"Stringency" refers to hybridization conditions that favor association of very similar sequences over sequences that differ. Hybridization conditions of moderate stringency are as follows: Filters containing DNA are pre-treated for 6 hours at 40° C. in a solution containing 10% to 35% formamide, 5×SSC, 50 mM Tris-HCl (pH 7.5), 5 mM EDTA, 0.02% PVP, 0.02% Ficoll, 0.02% BSA, and 500 mg/ml denatured salmon sperm DNA. Hybridizations are carried out in a solution containing 6×SSC, 50 mM Tris-HCl (pH 7.5), 1 mM EDTA, 0.1% PVP, 0.1% Ficoll, 1% BSA, and 500 ug/ml denatured salmon sperm DNA.

Hybridization conditions of high stringency are as follows: Filters containing DNA are pre-treated for 6 hours at 40° C. in a solution containing 36% to 50% formamide, 5×SSC, 50 mM Tris-HCl (pH 7.5), 5 mM EDTA, 0.02% PVP, 0.02% Ficoll, 0.02% BSA, and 500 mg/ml denatured salmon sperm DNA. Hybridizations are carried out in a solution containing 6×SSC, 50 mM Tris-HCl (pH 7.5), 1 mM EDTA, 0.1% PVP, 0.1% Ficoll, 1% BSA, and 500 ug/ml denatured salmon sperm DNA.

Hybridization conditions of very high stringency are as follows: Filters containing DNA are pre-treated for 6 hours at 40° C. in a solution containing 51% to 70% formamide, 5×SSC, 50 mM Tris-HCl (pH 7.5), 5 mM EDTA, 0.02% PVP, 0.02% Ficoll, 0.02% BSA, and 500 mg/ml denatured salmon sperm DNA. Hybridizations are carried out in a solution containing 6×SSC, 50 mM Tris-HCl (pH 7.5), 1 mM EDTA, 0.1% PVP, 0.1% Ficoll, 1% BSA, and 500 µg/ml denatured salmon sperm DNA.

Hybridization conditions are controlled such that the probes hybridize to nucleic acids that are identical to SEQ ID NO: 1. Under certain conditions, the probes also hybridize to nucleic acids that are 95% or 99% identical to SEQ ID NO: 1. Alternatively, conditions are such that the probes hybridize to nucleic acids at least 70%, 75%, 80%, 85%, 90%, 95%, 96%, 97%, 98%, or 99% identical to SEQ ID NO: 1. Typically, suitable probes are fragments which are significantly shorter than the full length sequence shown in SEQ ID NO: 1. Suitable fragments can contain from 5 to 100 nucleotides, preferably about 10 to about 80 nucleotides. The nucleotide sequence of such fragments is typically at least 70%, 75%, 80%, 85%, 90%, 95%, 96%, 97%, 98%, or 99% identical to a portion of the sequence shown in SEQ ID NO: 1 or its complement. Suitable fragments can contain modified bases such as inosine, methyl-5-deoxycytidine, deoxyuridine, demithylamino-5-deoxyuridine, or diamino-2,6 purine. Clones in libraries which contain insert genomic DNA fragments encoding a Mitrecin A polypeptide will hybridize to one or more of the fragments.

A nucleotide sequence encoding a polypeptide at least 90%, 95%, 96%, 97%, 98%, 99%, or 100% identical to SEQ ID NO: 2, fragments, analogs, derivatives, or variants described herein is useful for its ability to hybridize selectively, i.e., form duplex molecules with complementary stretches of other polypeptide genes. Depending on the application, a variety of hybridization conditions may be employed to achieve varying sequence identities. In specific aspects, nucleic acids are provided which comprise a sequence complementary to at least 10, 15, 25, 50, 100, 200, 250, 300, 350, 400, or 450 nucleotides of a Mitrecin A polypeptide described above. In specific embodiments, nucleic acids which hybridize to a Mitrecin A protein nucleic acid (e.g. having sequence SEQ ID NO: 1) under annealing conditions of low, moderate or high stringency conditions are within the scope of the invention.

For a high degree of selectivity, relatively stringent conditions are used to form the duplexes, such as, by way of example and not limitation, low salt and/or high temperature conditions, such as provided by hybridization in a solution of salt, e.g., 0.02 M to 0.15 M NaCl at temperatures of between about 50° C. to 70° C. For some applications, less stringent hybridization conditions are required, by way of example and not limitation such as provided by hybridization in a solution of 0.15 M to 0.9 M salt, e.g., NaCl, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated. By way of example and not limitation, in general, convenient hybridization temperatures in the presence of 50% formamide are: 42° C. for a probe which is 95 to 100% homologous to the target fragment, 37° C. for 90 to 95% homology and 32° C. for 70 to 90% homology. One aspect of the invention is directed to an isolated polynucleotide comprising a nucleic acid fragment which hybridizes, upon incubation in a solution comprising 50% formamide at about 37° C., to a DNA sequence which is complementary to SEQ ID NO:1 or fragments thereof, or a polynucleotide that is a codon-optimized coding region encoding a polypeptide of SEQ ID NO:2, or fragments thereof, wherein the nucleic acid fragment encodes a Mitrecin A polypeptide which is soluble when expressed in *E. coli.*

Other low, moderate and high stringency conditions are well known to those of skill in the art, and will vary predictably depending on the base composition and length of the particular nucleic acid sequence and on the specific organism from which the nucleic acid sequence is derived. For guidance regarding such conditions see, for example, Sambrook et al., Molecular Cloning, A Laboratory Manual, Second Edition, Cold Spring Harbor Press, N.Y., pp. 9.47-9.57 (1989); and Ausubel et al., Current Protocols in Molecular Biology, Green Publishing Associates and Wiley Interscience, N.Y. (1989).

Vectors, Expression Systems, and Methods of Producing

The present invention further provides a vector comprising a polynucleotide of the present invention. The term "vector," as used herein, refers to any of a number of nucleic acids into which a desired sequence may be inserted by restriction and ligation for transport between different genetic environments or for expression in a host cell. Vectors may be DNA or RNA. Vectors include, but are not limited to, plasmids, phage, phagemids, bacterial genomes, and virus genomes and virus-like particles. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. Certain vectors are capable of autonomous replication in a host cell into which they are introduced. Other vectors are integrated into the genome of a host cell upon introduction into the host cell, and thereby are replicated along with the host genome.

Any of a wide variety of suitable cloning vectors are known in the art and commercially available which can be used with appropriate hosts. The vector can be, for example, in the form of a plasmid, a viral particle, a phage, cosmid, etc. As used herein, the term "plasmid" refers to a circular, double-stranded construct made up of genetic material (i.e., nucleic acids), wherein the genetic material is extrachromosomal and replicates autonomously. A polynucleotide of the present invention may be in a circular or linearized plasmid or vector, or other linear DNA which may also be non-infectious and nonintegrating (i.e., does not integrate into the genome of host cells). Procedures for inserting a nucleotide sequence into an expression vector, and transforming or transfecting into an appropriate host cell and cultivating under conditions suitable for expression are generally known in the art, as described generally in Sambrook et al., Molecular Cloning, a Laboratory Manual, Cold Spring Harbor Press, Cold Spring Harbor, N.Y. (1989).

Also provided is a vector comprising a nucleic acid sequence encoding full-length or mature Mitrecin A polypeptides or fragments, variants, derivatives, or analogs thereof described herein. In particular, the present invention is directed to a vector comprising a nucleic acid fragment, which encodes a Mitrecin A polypeptide fragment described herein.

The present invention also includes a vector comprising a polynucleotide which encodes a polypeptide comprising, consisting essentially of, or consisting of an amino acid sequence at least 90%, 95%, 96%, 97%, 98%, 99%, or 100% identical to a SEQ ID NO: 2, a fragment thereof, a derivative thereof, or a variant thereof.

In another embodiment, the present invention is directed to a vector comprising a polynucleotide comprising, consisting essentially of, or consisting of a nucleotide sequence encoding a Mitrecin A polypeptide variant that lacks immunogenicity, wherein said polypeptide retains the antimicrobial activity.

In other embodiments, the present invention is further directed to a vector comprising a nucleic acid fragment, where the nucleic acid fragment is a fragment of a codon-optimized coding region operably encoding any Mitrecin A polypeptides described herein. Furthermore, the present invention includes a vector comprising any polynucleotides of the present invention.

Additional *Streptomyces*-derived coding or non-coding regions or endolysin coding regions may also be included on the vector, e.g., a plasmid, or on a separate vector, and expressed, either using native Mitrecin A codons or codons optimized for expression in the host in which the polypeptide is being expressed. When such a vector is delivered to a host, e.g., to a bacterial, plant or eukaryotic cell, or alternatively, in vivo to a tissue of the animal to be treated or immunized, the transcriptional unit will thus express the encoded gene product. The level of expression of the gene product will depend to a significant extent on the strength of the associated promoter and the presence and activation of an associated enhancer element, as well as the optimization of the coding region.

A variety of host-expression vector systems may be utilized to express the polypeptides of the present invention. The term "expression vector" refers to a vector that is capable of expressing the polypeptide of the present invention, i.e., the vector sequence contains the regulatory sequences required for polypeptide expression such as promoters, ribosome binding sites, etc. The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression may involve further processing steps to the RNA product of transcription, such as splicing to remove introns, and/or post-translational processing of a polypeptide product.

Vector-host systems include, but are not limited to, systems such as bacterial, mammalian, yeast, insect or plant cell systems, either in vivo, e.g., in an animal or in vitro, e.g., in mammalian cell cultures. The selection of an appropriate host is deemed to be within the scope of those skilled in the art from the teachings herein.

Host cells are genetically engineered (transduced or transformed or transfected) with the vectors of this invention as described above. Thus, one aspect of the invention is directed to a host cell comprising a vector which contains a polynucleotide of the present invention. The engineered host cell can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan. The term "transfect," as used herein, refers to any procedure whereby eukaryotic cells are induced to accept and incorporate into their genome isolated DNA, including but not limited to DNA in the form of a plasmid. The term "transform," as used herein, refers to any procedure whereby bacterial cells are induced to accept and incorporate into their genome isolated DNA, including but not limited to DNA in the form of a plasmid.

A large number of suitable vectors are known to those of skill in the art, and are commercially available. The following bacterial vectors are provided by way of example: pET, pET28, pBAD, pTrcHIS, pBR322, pQE70, pQE60, pQE-9 (Qiagen), phagescript, psiX174, pBluescript SK, pbsks, pNH8A, pNH16a, pNH18A, pNH46A (Stratagene), ptrc99a, pKK223-3, pKK233-3, pDR540, pBR322, pPS10, RSF1010, pRIT5 (Pharmacia); pCR (Invitrogen); pLex (Invitrogen), and pUC plasmid derivatives. However, any other plasmid or vector can be used as long as it is replicable and viable in the host. In addition, the lambda promoter provides high-level expression of recombinant proteins.

A suitable expression vector contains regulatory sequences which can be operably joined to an inserted nucleotide sequence encoding a Mitrecin A polypeptide. As used herein, the term "regulatory sequences" means nucleotide sequences which are necessary for or conducive to the transcription of an inserted sequence coding a Mitrecin A polypeptide by a host cell and/or which are necessary for or conducive to the translation by a host cell of the resulting transcript into the desired Mitrecin A polypeptide. Regulatory sequences include, but are not limited to, 5' sequences such as operators, promoters and ribosome binding sequences, and 3' sequences such as polyadenylation signals. Regulatory sequences may also include enhancer sequences or upstream activator sequences.

Generally, bacterial vectors will include origins of replication and selectable markers, e.g., the ampicillin, tetracycline, kanamycin, resistance genes of *E. coli*, permitting transformation of the host cell and a promoter derived from a highly-expressed gene to direct transcription of a downstream structural sequence. Such promoters include, but are not limited to, the T7 promoter, lambda (λ) promoter, T5 promoter, and lac promoter, or promoters derived from operons encoding glycolytic enzymes such as 3-phosphoglycerate kinase (PGK), acid phosphatase, or heat shock proteins, among others.

Once an expression vector is selected, the polynucleotide of the invention is cloned downstream of the promoter, often in a polylinker region. This plasmid is transformed into an appropriate bacterial strain, and DNA is prepared using standard techniques. The orientation and DNA sequence of the polynucleotide as well as all other elements included in the vector are confirmed using restriction mapping, DNA sequence analysis, and/or PCR analysis. Bacterial cells harboring the correct plasmid can be stored as cell banks.

Examples of mammalian host-expression systems include cell lines capable of expressing a compatible vector, for example, the COS, C127, 3T3, CHO, HeLa and BHK cell lines. Examples of suitable expression vectors include pWL-NEO, pSV2CAT, pOG44, pXT1, pSG (Stratagene) pSVK3, pBPV, pMSG, pSVL (Pharmacia), p75.6 (Valentis), pCEP (Invitrogen), pCEI (Epimmune), pZERO, pTrc99A, pUC19, pUC18, pKK223-3, pEX1, pCAL, pET, pSPUTK, pTrxFus, pFastBac, pThioHis, pTrcHis, and pLEx, pET-17b, pET-11a, pET-24a-d(+) and pET-9a pK233 (or any of the tac family of plasmids), pT7, lambda pSKF, and pET-28(a)+, vectors useful in yeast cells, including YIp, YRp, YCP, YEp and YLp plasmids as well as viral genomes from which to construct viral vectors such as Simian virus 40 (SV40), bovine papilloma virus, pox virus such as vaccinia virus, e.g., VV MVA, and parvovirus, including adeno-associated virus, retrovirus, herpesvirus, adenovirus, retroviral, e.g., murine leukemia virus and lentiviruses (e.g., human immunodeficiency virus), alphavirus, and picornavirus. References citing methods for the in vivo introduction of non-infectious virus genomes to animal tissues are well known to those of ordinary skill in the art. Any of a variety of methods known in the art can be used to insert a nucleotide sequence coding for a Mitrecin A polypeptide into a suitable expression vector.

Generally, mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. Such promoters may also be derived from viral sources, such as, e.g., human cytomegalovirus (CMV-IE promoter), herpes simplex virus type-1 (HSV TK promoter), the adenovirus late promoter; and the vaccinia virus 7.5K promoter, or can be derived from the genome of mammalian cells (e.g., metallothionein promoter). Nucleic acid sequences derived from the SV40 splice and polyadenylation sites can be used to provide the required nontranscribed genetic elements. A variety of transcription control regions are known to those skilled in the art. These include, without limitation, transcription control regions which function in animal cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from animal genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins). Similarly, a variety of translation control elements are known to those of ordinary skill in the art. These include, but are not limited to ribosome binding sites, translation initiation and termination codons, elements from picornaviruses (particularly an internal ribosome entry site, or IRES, also referred to as a CITE sequence).

Yeast host-expression systems include a yeast host (e.g., *Saccharomyces, Pichia, Hansenula, Kluyveromyces, Schizosaccharomyces, Schwanniomyces* and *Yarrowia*) transformed with recombinant yeast expression vectors containing polypeptide coding sequences, employing suitable vectors and control sequences. Suitable yeast expression vectors are known to those in the art and include, but are not limited to, e.g., pAL19, paR3, pBG1, pDBlet, pDB248X, pEA500, pFL20, pIRT2, pJK148, pON163, pSP1, pSP3, pUR19, pART1, pCHY21, REP41, pYZ1N, pSLF104, pSLF172, pDS472, pSGP572, pSLF1072, REP41MH-N, pFA6a-kanMX6, pARTCM, and pALL.

Insect host systems (e.g., *Trichoplusia, Lepidoptera, Spodoptera, Drosophila* and Sf9) infected with recombinant expression vectors (e.g., baculovirus, pDEST™10 Vector (Invitrogen), pMT-DEST48 Vector (Invitrogen), pFastBac Dual (Invitrogen), pIE1-neo DNA (Novagen), pIEX™-1 DNA (Novagen), containing polypeptide coding sequences of the present invention are also within the scope of the invention. See e.g., O'Reilly et al., Baculovirus Expression Vectors: A Laboratory Manual. Oxford Univ Press (1994).

Plant cell systems (e.g., *Arabidopsis*) infected with recombinant virus expression vectors (e.g., cauliflower mosaic virus, CaMV; tobacco mosaic virus, TMV) or transformed with recombinant plasmid expression vectors (e.g., Ti plasmid) containing polypeptide coding sequences of the present invention, containing polypeptide coding sequences are also within the scope of the invention. A list of vectors for a wide variety of plants can be found at http://www.arabidopsis.org/servlets/Order?state=catalog (viewed Jun. 20, 2006).

One of skill in the art will recognize that some of the above listed vectors are capable of replicating and expressing polypeptides in more than one type of host, e.g., the pOG44 plasmid can replicate and express polypeptides in both prokaryotic and eukaryotic cells.

In one embodiment, production of the polypeptides of the present invention can be achieved by culturing the host cells, expressing the polynucleotides of the present invention, and recovering the polypeptides. Determining conditions for culturing the host cells and expressing the polynucleotide are generally specific to the host cell and the expression system and are within the knowledge of one of skill in the art. In another embodiment, production of the polypeptides of the invention includes a synthetic method of making a polypeptide. The synthetic methods of making polypeptides are known in the art. In addition, appropriate methods for recovering the polypeptide of interest are known to those in the art, and include, but are not limited to, chromatography, filtration, precipitation, or centrifugation.

Compositions

Compositions that contain one or more polypeptides or polynucleotides of the invention are a further embodiment of the invention. Compositions of the invention also include a vector or a host cell comprising the polynucleotide of the invention.

The present invention relates to the use of Mitrecin A polypeptides provided by the present invention for the reduction of certain bacterial populations, including methods and compositions to prevent, inhibit, or reduce bacterial contamination or to treat, prevent, or ameliorate various bacterial infections. Thus, the present invention also relates to compositions and formulations comprising Mitrecin A polypeptides according to the present invention and the use of such compositions in prophylaxis or therapy of bacterial diseases, bacterial infections, bacterial contamination, or bacterial colonisations. In one aspect, a composition or formulation of the present invention is a decontamination composition or decontamination formulation. In another aspect, a composition or formulation of the present invention is a decolonisation composition or decolonisation formulation.

In some aspects, a composition or formulation of the present invention can be prepared as cream, lotion, liquid, solid, spray, solution, gel, emulsion, suspension, microemulsion, microcapsule, microgranule, ionic and/or non-ionic follicular dispersion, ointment, stick, or power. In other aspects, the composition or formulation of the invention can be formulated in the form of injections, oils, moisturizers, aerosols, or nasal inhalers by any method known in the art. These preparations are described in the following formulary known to all pharmaceutical chemists: Remington's Pharmaceutical Science, 15th Edition, 1975, Mack Publishing Company, Easton, Pa. 18042, Chapter 87: Blaug, Seymour.

In accordance with one embodiment of the invention, it may be desirable to contact a surface of a food with a polypeptide of the invention after processing or cooking. Additional embodiments include contacting the polypeptide of the invention with a non-food surface that is expected to come into contact with food, for example, a corner, table, ledge, food-processing machinery, or food packaging. This embodiment of the invention is a composition or formulation comprising a Mitrecin A polypeptide, a polynucleotide encoding a Mitrecin A polypeptide, a vector comprising the polynucleotide, or the host cell comprising the polynucleotide as a food preservative. Compositions of the invention when used on food or food packaging, for example, can be useful for preventing or inhibiting spoilage by bacteria on food or for enhancing or extending food storage life compared to a composition which does not comprise the Mitrecin A polypeptide, the Mitrecin A polynucleotide, the vector, or the host cell. In some embodiments, the composition of the present invention can further comprise one or more preservatives, which are useful for preventing or inhibiting spoilage by bacteria on food or for enhancing or extending food storage life.

Another embodiment of the invention provides a disinfectant or a sanitizing agent comprising a Mitrecin A polypeptide, a polynucleotide encoding a Mitrecin A polypeptide, a vector comprising the polynucleotide, or a host cell comprising the polynucleotide. In particular, a Mitrecin A polypeptide can be used to disinfect or sanitize medical tools, e.g., surgical tools, before or after a medical treatment, e.g., surgery, e.g., during hemodialysis. Similarly, premature infants and immune-compromised persons, or those subjects with need for a medical treatment, e.g., prosthetic devices, can be treated with a Mitrecin A polypeptide or polynucleotide of the present invention, either prophylactically or during acute infection. In the same context, nosocomial infections may be treated prophylactically or during acute phase with a Mitrecin A polypeptide of the present invention. For example, a disinfectant or sanitizing agent of the invention is used to treat or apply the area in which bacteria are growing or bacteria are expected to grow, e.g., hospital surfaces, tables, ledges, desks, floors, hospital machinery, and etc. In this embodiment, a Mitrecin A polypeptide of the present invention may be used as a disinfectant also in combination with other ingredients useful in a disinfecting solution like detergents, tensids, solvents, antibiotics, lantibiotics, or bacteriocins.

In certain embodiments, a composition of the invention includes an antibiotic comprising a Mitrecin A polypeptide, a polynucleotide encoding the Mitrecin A polypeptide, a vector comprising the polynucleotide, or a host cell comprising the polynucleotide. In one aspect, a composition of the invention is used to a subject who is suffering from an infection by pathogenic bacteria or is suspected of carrying pathogenic bacteria. In another aspect, a composition of the invention is used to a subject who is expected to come into a contact with pathogenic bacteria as a prophylactic measure.

A composition as disclosed herein may comprise more than one Mitrecin A polypeptide according to the present invention and/or may further comprise one or more additional agents. The one or more additional agents can potentiate the bactericidal activity of a Mitrecin A polypeptide of the invention or the bacteriostatic activity of a Mitrecin A polypeptide. The additional agent can be any agents in an amount that is effective to enhance the antimicrobial effect of a Mitrecin A polypeptide of the invention. Non-limiting examples of an additional agent include an enzyme, an antibiotic, an antifungal agent, an anti-viral agent, a bactericide, an analgesic, a destructive therapy agent, a bacteriocin, and an anti-inflammatory agent.

In some embodiments, a composition or formulation according to the present invention comprises a carrier suitable for delivering a Mitrecin A polypeptide or polynucleotide to the site of the bacterial growth, bacterial disease, bacterial infection or bacterial colonisation. "Carriers" as used herein include one or more acceptable carriers, excipients or stabilizers, which are non-toxic to the cell or the subject who may be exposed to a composition of the invention. In one embodiment, a carrier useful for the invention is a physiologically or pharmaceutically acceptable carrier. In one example, a physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polyoxyethylene sorbitol esters (TWEEN®), polyethylene glycol (PEG), and ethylene oxide and propylene oxide block copolymers (PLURONICs®).

In other embodiments, the carrier for a composition of the invention may be a stabilizing buffer for maintaining a suitable pH range. Compositions of the invention are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Any of the carriers for Mitrecin A polypeptides of the present invention may be manufactured by conventional means.

The compositions and formulations comprising a Mitrecin A polypeptide of the present invention as an active ingredient are applied in an effective amount when used in prophylaxis and therapy. The term "effective amount" refers to an amount of an active ingredient sufficient to achieve a desired effect without causing an undesirable side effect. In one example, an "effective amount" is an amount sufficient to kill one or more bacteria. In another example, an "effective amount" is an amount sufficient to prevent growth of one or more bacteria. In some cases, it may be necessary to achieve a balance between obtaining a desired effect and limiting the severity of an undesired effect. The amount of active ingredient used will vary depending upon the type of active ingredient and the intended use of the composition and/or formulation of the present invention. In a specific example, an effective amount of a Mitrecin A polypeptide is about 0.1 ng to about 100 mg, about 1 ng to about 50 mg, about 100 ng to about 10 mg, about 1 µg to about 10 mg, about 10 µg to about 1 mg, or about 100 µg to about 1 mg. In other embodiments, an effective amount of a Mitrecin A polypeptide is about 15 ng/ml to about 1.5 mg/ml.

In some embodiments, a mild surfactant in an amount effective to potentiate the antimicrobial effect of a Mitrecin A polypeptide may be used in or in combination with a therapeutic or prophylactic composition. Suitable mild surfactants include, inter alia, esters of polyoxyethylene sorbitan and fatty acids (Tween series), octylphenoxy polyethoxy ethanol (Triton X series), n-Octyl-p-D-glucopyranoside, n-Octyl-β-D-thioglucopyranoside, n-Decyl-D-glucopyranoside, n-Dodecyl-p-D-glucopyranoside, and biologically occurring surfactants, e.g., fatty acids, glycerides, monoglycerides, deoxycholate and esters of deoxycholate.

A mode of delivery of the composition comprising a Mitrecin A polypeptide includes, but is not limited to a smear, spray, a drink, a pill, a gargle, a chewing gum, a dietary supplement, a time-release patch, a liquid absorbed wipe, and combinations thereof.

One mode of delivery of the composition comprising a Mitrecin A polypeptide is a smear. Another mode of delivery of the composition comprising a Mitrecin A polypeptide is a spray. In some embodiments, a mode of delivery of the composition comprising a Mitrecin A polypeptide is a liquid absorbed wipe.

In some embodiments, preservatives may also be used in this invention and may comprise, for example, about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Compositions of the present invention can be formulated according to known methods. Suitable preparation methods are described, for example, in *Remington's Pharmaceutical Sciences,* 16th Edition, A. Osol, ed., Mack Publishing Co., Easton, Pa. (1980), and *Remington's Pharmaceutical Sciences,* 19th Edition, A. R. Gennaro, ed., Mack Publishing Co., Easton, Pa. (1995). Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives. Once formulated, the compositions of the invention can be administered directly to the subject. The subjects to be treated can be animals; in particular, human subjects can be treated.

Methods of Using and Regimens

The present invention includes a method of killing or preventing growth of one or more bacteria comprising contacting a Mitrecin A polypeptide with the one or more bacteria. The one or more bacteria can be present on a surface of an object, a plant, or an animal or within the object, plant, or animal. For example, the one or more bacteria, e.g., pathogenic bacteria, can be killed, or their growth can be inhibited, by applying a Mitrecin A polypeptide, a polynucleotide encoding the Mitrecin A polypeptide, a vector comprising the polynucleotide, a host cell comprising the vector, or a composition comprising the polypeptide or the polynucleotide on the surface of an object, a plant, or an animal. The object for example can be an environmental object, e.g., household furniture, e.g., a bathroom sink, or a hospital area, e.g., a hospital counter. In some aspects, the object is an inanimate item, for example, floors and/or flooring materials (e.g., Linoleum, tile, carpet, wood, paint, etc.), walls and/or wall covering materials (e.g., paint, wall paper, Formica, tile, etc.) windows and/or window materials (glass, Plexiglas, polycarbonate, etc.), water delivery system components (e.g., pumps, pipes, reservoirs), structural and/or cosmetic building materials (e.g., concrete, masonry, stucco, steel, stainless steel, aluminum, copper, nickel, cast iron, plastic, fiberglass, carbon fiber, Kevlar) counters, furniture, clothes, dishes, or combinations thereof.

In one aspect, the present invention is directed to a method of preventing, ameliorating, or treating a disease or disorder in a plant comprising contacting the plant with an effective amount of a Mitrecin A polypeptide, a polynucleotide encoding the Mitrecin A polypeptide, a vector comprising the polynucleotide, a host cell comprising the polynucleotide, or a composition comprising the Mitrecin A polypeptide, wherein the polypeptide, the polynucleotide, the vector, the host cell, or the composition prevents, ameliorates, or treats the disease or disorder in the plant. The disease or disorder in the plant may induce growth inhibition or retardation, less fruit formation, or a higher death rate of the plant compared to a plant without the disease or disorder.

In another aspect, the invention includes a method of promoting plant growth or disease resistance in a plant comprising contacting a Mitrecin A polypeptide, a polynucleotide encoding the Mitrecin A polypeptide, a vector comprising the polynucleotide, a host cell comprising the polynucleotide, or a composition comprising a Mitrecin A polypeptide, wherein the polypeptide, the polynucleotide, the vector, the host cell, or the composition promotes plant growth or disease resistance in the plant.

In other aspects, the method further comprises assessing prevention, amelioration, or treatment of a plant disease or disorder or assessing the plant growth promoting activity or plant disease resistance promoting activity.

A composition comprising a Mitrecin A polypeptide or a Mitrecin A polynucleotide can be formulated to be suitable for application to a plant. In one aspect, the composition is used to promote plant growth and/or promote disease resistance in plants. As used herein, the term "plant growth promoting activity" encompasses a wide range of improved plant properties, including, without limitation, improved nodulation (e.g. increased number of nodules), nitrogen fixation (e.g. increased nitrogen concentration as measured by mg $g^{-1}$ dry weight of plant material), increased leaf area, increased seed germination, increased leaf greenness (e.g. as measured by SPAD), increased photosynthesis ($\mu$mol $cm^{-2}$ $s^{-1}$), or an increase in accumulated dry-weight of the plant.

As used herein, the term "plant disease resistance promoting activity" or the like, encompasses, without limitation, increased resistance to pathogen attack or increased production of one or more secondary metabolites that function to improve the resistance of a plant to pathogen attack, as discussed herein.

An increase or improvement in plant growth or disease resistance means a statistically significant increase or improvement in the measured criterion of plant growth or disease resistance in a plant treated with a polypeptide according to the invention relative to an untreated control plant.

Assessment of the plant growth promoting activity of polypeptides may be accomplished by known methods. For instance, a polypeptide of interest may be applied by leaf spray or root irrigation to test plants, such as soybean plants. Plants may then be grown under controlled environment conditions (growth chamber or greenhouse) for e.g. about 40 days. At harvest, data may be collected concerning e.g. plant height, leaf greenness, leaf area, nodule number, nodule dry weight, shoot and dry root weight or length, nitrogen content and photosynthesis and compared to controls.

Assessment of plant disease resistance promoting activity of polypeptides may also be accomplished by known methods, such as by detecting or measuring a reduction in pathogen infestation of a plant, or indirectly by detecting or measuring increased production of one or more secondary metabolites that function to improve the resistance of a plant to pathogen attack. Exemplary secondary metabolites include lignification-related enzymes such as phenylalanine ammonia lyase (PAL), and tyrosine ammonia lyase (TAL), antioxidative enzymes such as peroxidase (POD), catalase (CAT), and superoxide dismutase (SOD), and total phenolic compounds. Various methods for detecting or measuring increases in enzyme activity levels in plants (e.g. PAL, TAL, POD, CAD and SOD) are known in the art and exemplary techniques are described in the examples herein. Similarly, techniques for determining concentrations or levels of total phenolic compounds are known and exemplary methods are described in the examples herein.

An increase or improvement in plant growth or disease resistance means a statistically significant increase or improvement in the measured criterion of plant growth or disease resistance in a plant treated with a polypeptide according to the invention relative to an untreated control plant.

In certain aspects, the present invention provides a method of preventing, ameliorating, or treating a disease or disorder in an animal comprising contacting the animal with an effective amount of a Mitrecin A polypeptide, a polynucleotide encoding the Mitrecin A polypeptide, a vector comprising the polynucleotide, a host cell comprising the polynucleotide, or a composition comprising the Mitrecin A polypeptide or the polynucleotide, wherein the polypeptide, the polynucleotide, the vector, the host cell, or the composition prevents, ameliorates, or treats the disease or disorder in the animal.

A Mitrecin A polypeptide or a composition comprising the Mitrecin A polypeptide according to the present invention is useful for treating and eliminating bacterial infestations anywhere, including upper respiratory infections, topical and systemic infections, vaginal infections, eye infections, ear infections, infections requiring parenteral treatment, as well as for the elimination of bacteria on any surface, including human skin and mucous membrane, e.g., the mucous membrane of the upper respiratory tract, e.g., the mucous membrane of the nasal cavity. A Mitrecin A polypeptide or a composition comprising the Mitrecin A polypeptide according to the present invention are particularly useful for the prophylaxis and treatment of upper respiratory infections, skin infections, wounds, burns, vaginal infections, eye infections, intestinal disorders and dental disorders. Specifically, the invention provides the application of Mitrecin A polypeptides for nasal and/or skin decolonisation of human and animals.

A Mitrecin A polypeptide of the invention may be administered to any subject afflicted with, diagnosed as afflicted with, or suspected of being afflicted with, an infection or contamination by bacteria susceptible to the Mitrecin A polypeptide. The invention also provides for the treatment or prevention of an opportunistic infection, such as that resulting from an undesirable growth of bacteria that are present in the microbial flora of a human subject or a non-human animal. An opportunistic infection may be the result of an immunosuppressed condition in a subject or the result of antibiotic treatment that alter the commensal flora of the genitourinary (GU) or gastrointestinal (GI) tract. Thus the disclosure also provides for the treatment or prophylaxis of immunosuppressed subjects and subjects exposed to other pharmaceutical agents. A Mitrecin A polypeptide with its anti-bacterial activity may be used in combination with another anti-bacterial or anti-microbial agent, such as an antibiotic or anti-fungal agent as non-limiting examples. An "anti-microbial agent" is an agent or compound that can be used to inhibit the growth of, or to kill, single-celled organisms. Anti-microbial agents include antibiotics, chemotherapeutic agents, antibodies (with or without complement), and chemical inhibitors of DNA, RNA, protein, lipid, or cell wall synthesis or functions.

Additionally, and in anticipation of a possible emergence of bacterial resistance to a Mitrecin A polypeptide, there can be a concomitant compromise of the organisms' virulence or fitness where the Mitrecin A polypeptide targets the virulence or fitness factor of the targeted bacteria. Because a major, but non-limiting, mechanism by which a bacterium may become resistant to a Mitrecin A polypeptide is the loss of its receptor for the Mitrecin A polypeptide, the targeting of a virulence or fitness factor as disclosed herein provides many advantages over traditional antibiotics and bacteriophages. The resistance to traditional antibiotics and bacteriophages can result from many different mechanisms other than loss of the receptor or target molecule of the antibacterial agent. As non-limiting examples, a Mitrecin A polypeptide of the invention would not be subject to a bacterial efflux pump to remove the Mitrecin A polypeptide from the cellular environment and would not be subject to a bacterial nucleic acid deactivation mechanism.

In one aspect of the present invention, Mitrecin A polypeptides are applied in a method for the treatment or prophylaxis of one or more bacteria, which are selected from the group consisting of a Gram-positive bacterium, a Gram-negative bacterium, or both. Examples of Gram-positive target bacteria that can be killed or inhibited include, but are not limited to, *Streptomyces avermitilis, Streptomyces coelicolor, Streptomyces lividans, Streptomyces venezuelae, Nocardia salmonicida, Nocardia vaccinii, Rhodococcus marinonascens, Bacillus megaterium, Bacillus subtilis, Bacillus cereus, Enterococcus faecalis, Micrococcus luteus, Staphylococcus aureus, Streptococcus* sp., *Streptococcus pyogenes, Listeria monocytogenes, Clostridium perfringens, Clostridium botulinum, Lactococcus cremoris, Lactobacillus* sp., and *Leuconostoc* sp. Thus, a Gram-positive target bacterium can be selected from the group consisting of *Streptomyces avermitilis, Streptomyces coelicolor, Streptomyces lividans, Streptomyces venezuelae, Nocardia salmonicida, Nocardia vaccinii, Rhodococcus marinonascens, Bacillus megaterium, Bacillus subtilis, Bacillus cereus, Enterococcus faecalis, Micrococcus luteus, Staphylococcus aureus, Streptococcus* sp., *Streptococcus pyogenes, Listeria monocytogenes, Clostridium perfringens, Clostridium botulinum, Lactococcus cremoris, Lactobacillus* sp., and *Leuconostoc* sp.

Examples of Gram-negative target bacteria include, but are not limited to, *Escherichia coli, Klebsiella pneumoniae, Salmonella typhimurium, Salmonella enterica, Campylobacter jejuni, Yersinia enterocolitica, Yersinia pseudotuberculosis, Vibrio cholerae, Vibrio parahaemolyticus, Vibrio vulnificus, Aeromonas hydrophila, Plesiomonas shigelloides, Shigella sonnei, Shigella flexneri, Enterobacter aerogenes, Flavobacterium* sp., *Acinetobacter* sp., and *Proteus* sp. Thus, a Gram-negative target bacterium can be selected from the group consisting of *Escherichia coli, Klebsiella pneumoniae, Salmonella typhimurium, Salmonella enteritidis, Campylobacter jejuni, Yersinia enterocolitica, Yersinia pseudotuberculosis, Vibrio cholerae, Vibrio parahaemolyticus, Vibrio vulnificus, Aeromonas hydrophila, Plesiomonas shigelloides, Shigella sonnei, Shigella flexneri, Enterobacter aerogenes, Flavobacterium* sp., *Acinetobacter* sp., and *Proteus* sp.

In some embodiments, the target bacterium is *Vibrio* sp., *Salmonella* sp., *Yersinia* sp., or *Bacillus* sp. In a particular embodiment, the target bacterium is *Vibrio cholerae, Salmonella enterica, Yersinia pseudotuberculosis, Shigella sonnei, Aeromonas hydrophila* or *Bacillus subtilis*. In other embodiments, the target bacterium is *S. aureus, S. epidermidis, S. haemolyticus, S. simulans, S. saprophyticus, S. chromogenes, S. hyicus, S. warneri* and/or *S. xylosus*. The subject may be a human subject or an animal, in particular animals used in livestock farming and/or dairy farming such as cattle and pigs. The method of treatment encompasses the application of a Mitrecin A polypeptide of the present invention to the site of infection or site to be prophylactically treated against infection in a sufficient amount. In particular, the method of treatment may be for the treatment or prophylaxis of infections, in particular by *Staphylococcus aureus*, of the skin, of soft tissues, of bacteremia and/or endocarditis.

Other aspects of the present invention includes a method of detecting or measuring presence of one or more pathogenic bacteria in a sample comprising contacting an effective amount of a Mitrecin A polypeptide, a polynucleotide encoding the Mitrecin A polypeptide, a vector comprising the polynucleotide, a host cell comprising the polynucleotide, or a composition comprising the Mitrecin A polypeptide. In one embodiment, the sample is a tissue of an animal or a plant. In another embodiment, the sample is an environmental sample, e.g., soil or water. In one embodiment, target bacteria can be captured using a Mitrecin A polypeptide and detected with a secondary reagent such as an antibody. Suitable targets include, but are not limited to, the targets in Table 4.

TABLE 4

Examples of Target Pathogen

| Target Pathogen | Disease |
| --- | --- |
| Bacillus anthracis | Anthrax |
| Multi-Drug Resistant Staphylococcus aureus | MRSA |
| Yersinia pestis | Plague |
| Francisella tularensis | Tularemia |
| Vibrio cholerae | Cholera |
| Salmonella enterica | Salmonellosis |
| Shigella sonnei | Shigellosis |
| Aeromonas hydrophila | Gastroenteritis |

In some embodiments, a Mitrecin A polypeptide of the invention is formulated with a "pharmaceutically acceptable" excipient or carrier. Such a component is one that is suitable for use with humans, animals, and/or plants without undue adverse side effects. Non-limiting examples of adverse side effects include toxicity, irritation, and/or allergic response. The excipient or carrier is typically one that is commensurate with a reasonable benefit/risk ratio. In many embodiments, the carrier or excipient is suitable for topical or systemic administration. Non-limiting pharmaceutically suitable carriers include sterile aqueous or non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

A Mitrecin A polypeptide of the invention is typically used in an amount or concentration that is "safe and effective," which refers to a quantity that is sufficient to produce a desired therapeutic response without undue adverse side effects like those described above. A Mitrecin A polypeptide may also be used in an amount or concentration that is "therapeutically effective," which refers to an amount effective to yield a desired therapeutic response, such as, but not limited to, an amount effective to slow the rate of bacterial cell division, or to cause cessation of bacterial cell division, or to cause death or decrease rate of population growth of the bacteria. The safe and effective amount or therapeutically effective amount will vary with various factors but may be readily determined by the skilled practitioner without undue experimentation. Non-limiting examples of factors include the particular condition being treated, the physical condition of the subject, the type of subject being treated, the duration of the treatment, the nature of concurrent therapy (if any), and the specific formulations employed.

A Mitrecin A polypeptide of the disclosure may be administered to a subject by any suitable means. Non-limiting examples include topical or localized administration as well as pulmonary (inhalation), gastrointestinal, by catheter or drip tube, or systemic administration to a subject. Representative, and non-limiting, examples of systemic administration include intraperitoneal and intravenous administration. In some embodiments, contact between a Mitrecin A disclosed herein and a target bacterial population results in a decrease in the population of at least 10, at least 100, at least 1000, or at least 10,000, or more, fold decrease relative to the absence of the bacteriocin. In other embodiments, the contact may result in a decrease in detectability of the bacteria by at least 5, at least 10, at least 20, at least 30, at least 40, or at least 50, or more, fold relative to the absence of the bacteriocin.

In some embodiments, means of application of Mitrecin A polypeptide(s) of the invention include, but are not limited to, direct, indirect, carrier and special means or any combination of means. Direct application of a Mitrecin A polypeptide may be by nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or any combination of these and similar methods of application. The forms in which a Mitrecin A polypeptide may be administered include but are not limited to powders, sprays, liquids, gels, ointments, and aerosols. It is most probable that exposure to the bacteria will be through the nose. Preferred are sprays, liquids, gels, ointments, and aerosols.

The dosage and route of administration used in a method of treatment (or prophylaxis) according to the present invention depends on the specific target bacteria. The route of administration may be, for example, oral, topical, nasopharyngeal, parenteral, intravenous, rectal or any other route of administration.

The effective dosage rates or amounts of a Mitrecin A polypeptide(s) to treat the infection will depend in part on whether the Mitrecin A polypeptide will be used therapeutically or prophylactically, the duration of exposure of the recipient to the infectious bacteria, the size and weight of the individual, etc. The duration for use of the composition containing a Mitrecin A polypeptide also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. The concentration of the active units of chimeric polypeptide that may provide for an effective amount or dosage of a Mitrecin A polypeptide may be in the range of 10 units/ml to 500,000 units/ml of fluid in the wet or damp environment of the nasal and oral passages, and topically as well and possibly in the range of 10, 20, 30, 40, 50, 60, 70, 80, 90, or 100 units/ml to 50,000 units/ml. Representative values thus include about 200 units/ml, 300 units/ml, 500 units/ml, 1,000 units/ml, 2,500 units/ml, 5,000 units/ml, 10,000 units/ml, 20,000 units/ml, 30,000 units/ml, and 40,000 units/ml. More specifically, time exposure to the active polypeptide units may influence the desired concentration of active polypeptide units per ml. It should be noted that carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depend on the nature of infection, whether treatment is to be prophylactic or therapeutic, and other variables. Thus, the number of dosages will be dependent upon the circumstances and can range from 1 to 4 times per day or more, with durations from one day to multiple weeks.

The route of administration is in accordance with known methods. When treating a bacterial exposure or infection, a Mitrecin A polypeptide may be administered in any suitable fashion, including topical administration or through the oral or nasal cavity. For topical application a polypeptide of the present invention may be administered by way of a lotion or plaster. For nasopharyngeal application a Mitrecin A polypeptide according to the present invention may be formulated in saline in order to be applied via a spray to the nose. Dosages and desired drug concentrations of pharmaceutical compositions of the present invention may vary depending on the particular use envisioned. The determination of the appropriate dosage or route of administration is well within the skill of an ordinary physician.

Kits

The polypeptide or polynucleotide compositions of this invention can be provided in kit form together with a means for administering the polypeptide, polynucleotide, or composition of the present invention. In some embodiments, the kit can further comprise instructions for vaccine administration.

Typically the kit would include desired composition(s) of the invention in a container, e.g., in unit dosage form and instructions for administration. Means for administering the composition of the present invention can include, for example, a sterile syringe, an aerosol applicator (e.g., an inhaler or any other means of nasal or pulmonary administration), a gel, a cream, a transdermal patch, transmucosal patch (or any other means of buccal or sublingual administration), or an oral tablet. In some embodiments, the kit of the present invention contains two or more means for administering the polypeptides, polynucleotides, vectors, or compositions of the present inventions, e.g., two or more syringes.

In some embodiments, the kit may comprise more than one container comprising the polypeptide, polynucleotide, or composition of the present invention. For example, in some embodiments the kit may comprise a container containing a priming component of the present invention, and a separate container comprising the boosting component of the present invention.

Optionally associated with such container(s) can be a notice or printed instructions. For example, such printed instructions can be in a form prescribed by a governmental agency regulating the manufacture, use or sale of pharmaceuticals or biological products, which notice reflects approval by the agency of the manufacture, use or sale for human administration of the present invention. "Printed instructions" can be, for example, one of a book, booklet, brochure or leaflet.

The kit can also include a storage unit for storing the components (e.g., means of administering, containers comprising the polypeptides, polynucleotides, or compositions of the present inventions, printed instructions, etc.) of the kit. The storage unit can be, for example, a bag, box, envelope or any other container that would be suitable for use in the present invention. Preferably, the storage unit is large enough to accommodate each component that may be necessary for administering the methods of the present invention.

The present invention can also include a method of delivering a polypeptide, polynucleotide, or composition of the present invention to an animal such as a human in need thereof, the method comprising (a) registering in a computer readable medium the identity of an administrator (e.g., a physician, physician assistant, nurse practitioner, pharmacist, veterinarian) permitted to administer the polypeptide, polynucleotide, vector, or composition of the present invention; (b) providing the human with counseling information concerning the risks attendant the polypeptide, polynucleotide, vector, or composition of the present invention; (c) obtaining informed consent from the human to receive the polypeptide, polynucleotide, vector, or composition of the present invention despite the attendant risks; and (e) permitting the human access to the polypeptide, polynucleotide, vector, or composition of the present invention.

Having now generally described the inventive subject matter, the same will be more readily understood through reference to the following examples which are provided by way of illustration, and are not intended to be limiting of the disclosure, unless specified.

EXAMPLES

Example 1: Bacterial Strains, Media, and Bacteriocin Production

*Streptomyces*, a medically and industrially important genus of soil bacteria, produce many useful antibiotics and enzymes, contain large prokaryotic genomes, and produce secondary metabolites with exceptional functionality. The previously uncharacterized *Streptomyces* sp. strain 212 was isolated on environmental extract medium from a soil sample of Rainbow Bluff, a woodland bluff of Lynn, Ala. The strain was one of 45 isolates demonstrating lytic activity against heat-killed bacterial substrate. One of the lytic enzyme producers, strain 212, resembled the genus *Streptomyces* in colony morphology, carbohydrate utilization, and 16S rRNA gene sequence. The total bacteriocin activity of strain 212 was measured against both Gram-negative and Gram-positive bacteria using zymogram (renaturing SDS-PAGE) analysis (FIG. 1) and the line inoculum assay.

*Streptomyces*, sp. strain 212 was monitored over three weeks for its carbohydrate utilization. The carbohydrate utilization assay was used to define the metabolic capabilities of this bacterium as compared to other *Streptomyces* species. Table 5 shows various carbohydrate consumptions by *Streptomyces* sp. strain 212 during three weeks.

TABLE 5

| Carbohydrate Consumption | | | |
|---|---|---|---|
| Carbohydrates | Week 1 | Week 2 | Week 3 |
| Adonitol | − | − | − |
| Arabinose | + | + | + |
| Dextrin | +/− | + | + |
| Dextrose | + | + | + |
| Fructose | − | + | + |
| Galactose | + | + | + |
| Inositol | − | − | + |
| Inulin | +/− | + | + |
| Lactose | − | − | − |
| Maltose | + | + | + |
| Mannitol | − | + | + |
| Mannose | + | + | + |
| Sorbitol | − | − | − |
| Xylose | + | + | + |

Example 2: Phylogenetic Analysis of *Streptomyces* sp. Strain 212 16S rRNA Sequence Phylogenetic relatedness of Strain 212 to other closely related bacteria was assessed using partial 16S rRNA gene sequences identified with BLASTn. The reference sequences and strain 212 sequence were aligned in BioEdit Sequence Alignment Editor using CLUSTAL W. The neighbor-joining algorithm of PAUP* version 4.0 was used to infer the phylogenetic relatedness of the sequences. Tree topologies were calculated by bootstrap analyses based on 1000 resamplings. FIG. 2 shows the neighbor-joining cladogram based on this analysis which related *Streptomyces* sp. strain 212 and other *Streptomyces* species.

Example 3: Genome Sequencing and Annotation

Genomic DNA from Strain 212 was subjected to de novo genome sequencing and assembly at The Institute for Genome Sciences (IGS) Genomics Resource Center at the University of Maryland using the 454 GS/FLX pyrosequencing platform and GS de novo sequence assembly software, Newbler. The putative genes within the draft-quality genome were annotated using the IGS Annotation Engine. Open reading frames (ORFs) were identified by Glimmer 3 algorithm, while tRNA and rRNA genes were detected by tRNAscan-SE and RNAmmer, respectively. The genome of the streptomycete, estimated by pyrosequencing, is approximately 10 Mbp with a GC content of 68%. Comparison of the Mitrecin A gene sequence to other known genes using BLASTn indicates similarity to bacteriophage endolysin genes.

Example 4: Gene Synthesis, Expression, and Mitrecin A Purification

Annotation of the *Streptomyces* sp. strain 212 genome identified a suite of putative bacteriolytic genes, including the gene for Mitrecin A. The gene for Mitrecin A was fused with a C-terminal 6-histidine tag sequence. Mitrecin A was subsequently synthesized and expressed as seen in FIG. 3A. The first step in the isolation was a partial purification by one-step immobilized metal ion affinity chromatography to a purity of 90%, as estimated using the 2100 Bioanalyzer platform. Partially purified protein was stored at −80° C. in 50 mM Tris (pH 9.0), 0.5 mM L-arginine, and 10% glycerol. Mitrecin A was further purified using an HPLC system fitted with a Superdex 75 size exclusion column. Mitrecin A was determined to be isolated from contaminates using 12% SDS-PAGE, western blot, and Bioanalyzer analyses. The N-terminus of the purified enzyme was sequenced using Edman degradation at the Iowa State University Protein Facility. FIG. 3B shows the 14.3 kDa purified protein as visualized by an anti-His western blot.

Example 5: Effects of Temperature, Salinity, and pH on Mitrecin A Activity

For each stressor, residual enzyme activity was assessed using a modified version of the quantitative dye-release assay described by Zhou et al. using *Y. pseudotuberculosis* as cell substrate (Zhou et. al, Analytical Biochemistry 171: 141-144 (1988)). Thermal stability of Mitrecin A was tested after challenge against various temperatures (4-95° C.) for 30 min, and the results are displayed in FIG. 4A. FIGS. 4B and 4C show the results of testing the stability of the enzyme in various pH and saline conditions in dye-release assays over 16 h incubations at 37° C. Mitrecin A displays the greatest bacteriolytic activity at elevated pH values ranging from 7 to 11, in saline conditions of 1.5%, and at ambient temperatures.

Example 6: Functional Assays of Mitrecin A Activity

The spectrum of bacteriolytic activity against various Gram-positive and Gram-negative bacteria was assessed using slide diffusion assays, an example of which is shown in FIG. 5. The residual viability of the *Y. pseudotuberculosis* indicator organism in the presence of various concentrations of Mitrecin A was also assayed by serial dilution and colony forming unit assays after 16 h incubation at 37° C., as shown in FIG. 6. Table 6 summarizes the inhibitory spectrum of Mitrecin A, which includes bacteriolytic activity against the medically important genera of *Salmonella, Vibrio*, and *Yersinia*.

TABLE 6

Inhibitory Spectrum of Mitrecin A

| Gram-Negative Bacteria | Lysis | Gram-Positive Bacteria | Lysis |
|---|---|---|---|
| *Francisella philomiragia* | Negative | *Bacillus cereus* | Negative |
| *Salmonella enterica* | Positive | *Bacillus thuringiensis* | Negative |
| *Vibrio cholerae* | Positive | *Bacillus subtilis* | Negative |
| *Yersinia pseudotuberculosis* | Positive | *Staphylococcus aureus* | Negative |
| *Aeromonas hydrophila* | Positive | | |
| *Shigella sonnei* | Positive | | |
| *Escherichia coli* DH5α | Positive | | |

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. A method of ameliorating or treating a disease or disorder in an animal, the method comprising contacting the animal with a formulation comprising an effective amount of an isolated polypeptide comprising an amino acid sequence at least 90% identical to the full-length sequence of SEQ ID NO: 2 or a fragment thereof that comprises amino acids 54 to 73 (Conserved Region 1) of SEQ ID NO: 2, wherein contacting the animal with the formulation ameliorates or treats the disease or disorder in the animal, and wherein the disease or disorder is an infection caused by a Gram negative bacteria.

2. The method of claim 1, wherein the isolated polypeptide or fragment is conjugated to a second polypeptide.

3. The method of claim 1, wherein the amino acid sequence of the isolated polypeptide is that of SEQ ID NO: 2.

4. The method of claim 1, wherein the amino acid sequence of the isolated polypeptide is that of the fragment of SEQ ID NO: 2 that comprises amino acids 54 to 73 (Conserved Region 1) of SEQ ID NO: 2.

5. The method of claim 4, wherein the fragment further comprises amino acids 81 to 90 (Conserved Region 2) of SEQ ID NO: 2, amino acids 106 to 121 (Conserved Region 3) of SEQ ID NO: 2, or both.

6. The method of claim 1, wherein the Gram-negative bacteria comprise at least one member of the group consisting of *Escherichia coli, Klebsiella pneumoniae, Salmonella typhimurium, Salmonella enterica, Campylobacter jejuni, Yersinia enterocolitica, Yersinia pseudotuberculosis, Vibrio cholerae, Vibrio parahaemolyticus, Vibrio vulnificus, Aeromonas hydrophila, Plesiomonas shigelloides, Shigella son-*

*nei, Shigella flexneri, Enterobacter aerogenes, Flavobacterium* sp., *Acinetobacter* sp., *Shigella* sp., *Aeromonas* sp., and *Proteus* sp.

7. The method of claim 1, wherein the infection is an upper respiratory infection, skin infection, wound infection, burn infection, vaginal infection, eye infection, intestinal disorder, or dental disorder.

8. The method of claim 1, wherein the animal is a human.

9. The method of claim 1, wherein the animal is a non-human animal.

10. The method of claim 1, wherein the formulation is sterile.

11. The method of claim 1, wherein the formulation is formulated as a topical cream or lotion.

12. The method of claim 1, wherein the formulation is formulated as a gargle, a pill, or a chewing gum.

13. The method of claim 1, wherein the formulation is formulated as a drink or a dietary supplement.

14. The method of claim 6, wherein the Gram-negative bacteria comprise at least one member of the group consisting of *Salmonella enterica, Yersinia pseudotuberculosis, Shigella sonnei*, and *Aeromonas hydrophila*.

15. The method of claim 1, wherein the formulation is formulated as a spray, a powder, or a wipe.

\* \* \* \* \*